(12) United States Patent
Beer et al.

(10) Patent No.: US 9,878,030 B2
(45) Date of Patent: Jan. 30, 2018

(54) BVDV VACCINE

(75) Inventors: Martin Beer, Greifswald-Insel Riems (DE); Ilona Reimann, Greifswald-Insel Riems (DE); Patricia Koenig, Greifswald-Insel Riems (DE)

(73) Assignee: Intervet Inc., Madison, NJ (US)

( * ) Notice: Subject to any disclaimer, the term of this patent is extended or adjusted under 35 U.S.C. 154(b) by 42 days.

(21) Appl. No.: 13/825,050

(22) PCT Filed: Sep. 21, 2011

(86) PCT No.: PCT/EP2011/066377
§ 371 (c)(1),
(2), (4) Date: Mar. 19, 2013

(87) PCT Pub. No.: WO2012/038454
PCT Pub. Date: Mar. 29, 2012

(65) Prior Publication Data
US 2013/0195892 A1    Aug. 1, 2013

Related U.S. Application Data

(60) Provisional application No. 61/385,010, filed on Sep. 21, 2010.

(30) Foreign Application Priority Data

Sep. 21, 2010    (EP) .................................... 10177931

(51) Int. Cl.
*A61K 39/12* (2006.01)
*C12N 7/00* (2006.01)
*A61K 39/295* (2006.01)
*C07K 14/18* (2006.01)
*A61K 39/40* (2006.01)
*C07K 14/005* (2006.01)
*A61K 39/42* (2006.01)
*A61K 39/00* (2006.01)

(52) U.S. Cl.
CPC ............ *A61K 39/12* (2013.01); *A61K 39/295* (2013.01); *A61K 39/40* (2013.01); *A61K 39/42* (2013.01); *C07K 14/005* (2013.01); *A61K 2039/5254* (2013.01); *A61K 2039/552* (2013.01); *A61K 2039/70* (2013.01); *C12N 2770/24322* (2013.01); *C12N 2770/24334* (2013.01); *C12N 2770/24362* (2013.01)

(58) Field of Classification Search
CPC ............ A61K 2039/5254; A61K 39/42; A61K 2039/552; C12N 2770/24334; C12N 2770/24362
USPC ........................................................ 424/159
See application file for complete search history.

(56) References Cited

U.S. PATENT DOCUMENTS 6,001,613 A     12/1999  Donis et al.
2003/0104612 A1*  6/2003  Cao et al. .................. 435/320.1
2009/0068223 A1*  3/2009  Meyers et al. ............. 424/201.1

FOREIGN PATENT DOCUMENTS

CN    101360510 A       2/2009
WO    1999064604 A3     1/2000
WO    2012038454 A1     3/2012

OTHER PUBLICATIONS

Meyers et al., Bovine viral diarrhea virus: prevention of persistent fetal infection by a combination of two mutations affecting E(rns) RNase and N(pro) protease, 2007, 81(7):3327-3338.*
Cortese et al., "Protectiong of pregnant cattle and their fetuses against infection with bovine viral diarrhea virus type 1 by use of a modified-live virus vaccine", 1998, AM J Vet Res., 1998, 59(11):pdf p. 1.*
Fulton et al., "Bovine viral diarrhea virus types 1 and 2 antibody response in calves receiving modified live virus or inactivated vaccines", Vaccine, 2001, pp. 264-274, vol. 19.
Geiser et al., "Integration of PCR fragments at any specific site within cloning vectors without the use of restriction enzymes and DNA ligase", 2001, Biotechniques, pp. 88-90, 92, vol. 31.
Meyers et al., "Bovine viral diarrhea virus: prevention of persistent fetal infection by a combination of two mutations affecting Erns RNase and Npro protease", Journal of Virology, 2007, pp. 3327-3338, vol. 81, No. 7.
Meyers et al., "Recovery of cytopathogenic and noncytopathogenic bovine viral diarrhea viruses from cDNA constructs", Journal of Virology, 1996, pp. 8606-8613, vol. 70, No. 12.
Schmitt et al., "Expression of bovine viral diarrhoea virus glycoprotein E2 by bovine herpesvirus-1 from a synthetic ORF and incorporation of E2 into recombinant virions", Journal of General Virology, 1999, pp. 2839-2848, vol. 80.
Wolfmeyer et al., "Genomic (5'UTR) and serological differences among German BVDV field isolates", Archives of Virology, 1997, pp. 2049-2057, vol. 142.
International Search Report for corresponding PCT/EP2011/066377, dated Feb. 3, 2012.
Cortese et al., Protection of pregnant cattle and their fetuses against infection with bovine viral diarrhea virus type 1 by use of modified-live virus vaccine, AJVR, 1998, pp. 1409-1413, vol. 59: No. 11.
Fairbanks, K, et al., Evaluation of a Modified Live Virus Type-1a Bovine Viral Diarrhea Virus Vaccine (Singer Strain) against a Type-2 (Strain 890) Challenge, Veterinary Therapeutics, 2003, pp. 24-34, vol. 4, No. 1.
Resvac 4/Somubac (Zoetis Inc.); Bovine Rhinotracheitis—Virus Diarrhea-Parainfluenza-Respiratory Syncytial Virus Vaccine. Compendium of Veterinary Products—Resvac 4/Somubac. www.zoetis.com. Apr. 2016. pp. 1-4.
Mayer, D. et al., Attenuation of classical swine fever virus by deletion of the viral Npro gene, Vaccine, 2004, pp. 317-328, 22.

* cited by examiner

*Primary Examiner* — Barry A Chestnut

(57) ABSTRACT

The present invention relates to BVD virus and to its uses, to vaccines and combination vaccines comprising such a virus, their use as a medicament, their use in the treatment of Bovine Viral Diarrhea and to methods for the preparation of such vaccines.

16 Claims, 9 Drawing Sheets

Figure 2:
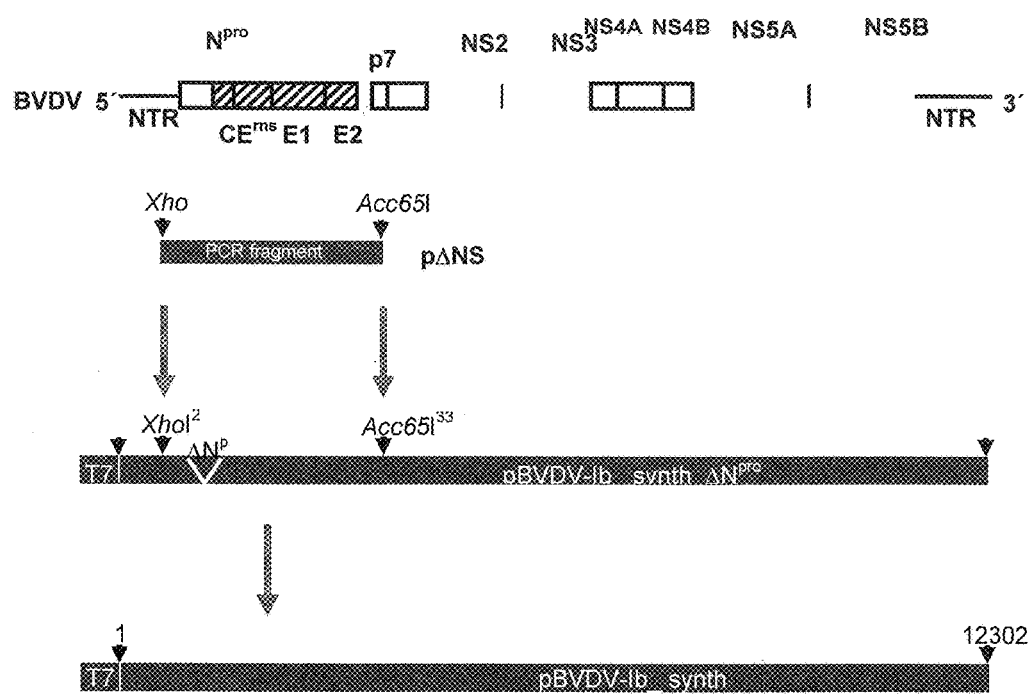

Vaccinees:
4 animals

Controls:
4 animals

♂, Holstein-Frisean, 4-6 months of age
negative for pestivirus antibodies d 0          d 52          d 80 vaccination     challenge     end of study
mock

Figure 8

NCP7 ΔN$^{pro}$
4 animals

NCP7
4 animals

♂, Holstein-Frisean, primipara
pregnancy ~day 70
negative for pestivirus antibodies
negative for pestiviruses day of gestation   d 0      d 71-d79      ~d 160 insemination infection      12 weeks p. i.
end of study

Figure 9

```
●────☆────────☆──────────────★──────────────────●
day 0      day 25          day 60              day 89
```

| 1st 890ΔC | 2nd 890 ΔC | challenge infection | |
| | 1st cp7 ΔN | | |
| | 890 ΔN/cp7 ΔN | HI916 | |
| | 890 ΔN | | | sampling and clinical monitoring    ☆ 10 days    ★ 14 (resp.16) days

Figure 10

```
●────☆────────☆──────────────★──────────────────●
day -56    day -28         day 0               day 28
```

1st vaccination        2nd vaccination      challenge infection       end of trial cp7ΔNpro              v890FLΔNpro          HI916 sampling and clinical monitoring    ☆ no sampling    ☆ 8 days    ★ 14 (resp.15) days

Figure 11

```
       ☆                        ✹
●━━━━━━━━━━━━━━━━━━━━━━━━━━━━━━━━━━━━━━━━━━━━━━━━━▶●
day -28                      day 0                  day 21
vaccination              challenge infection       end of trial
cp7ΔN_E2CS                    HI916
cp7ΔN_E2CS/cp7ΔN sampling and clinical monitoring   ☆ 11 days   ✹ 14 (resp.15) days
```

BVDV VACCINE

CROSS-REFERENCE TO RELATED APPLICATIONS

This application is a national stage entry under 35 U.S.C. §371 of PCT/EP2011/066377, filed on Sep. 21, 2011, which claims priority to U.S. Provisional Application No. 61/385,010, filed on Sep. 21, 2010, and EP Application No. 10177931.2, filed on Sep. 21, 2010. The content of PCT/EP2011/066377 is hereby incorporated by reference in its entirety.

The present invention relates to BVD virus and to its uses, to vaccines and combination vaccines comprising such a virus, their use as a medicament, their use in the treatment of Bovine Viral Diarrhoea and to methods for the preparation of such vaccines.

Bovine viral diarrhea virus (BVDV), a member of the genus *Pestivirus* within the family Flaviviridae is the causative agent of bovine viral diarrhea, an economically important disease of cattle world-wide. Pestiviruses can be divided into two different biotypes, cytopathogenic (cp) and non cytopathogenic (ncp) viruses, respectively. Genetically and structurally closely related virus species are Classical Swine Fever Virus (CSFV) and the ovine Border Disease Virus (BDV).

The major economic losses caused by BVDV infections are due to reduced milk production, growth retardation, reduced reproductive performance, and increased occurrence of other diseases, such as Shipping Fever. Reduced reproductive performance is caused i.a. by reduced fertility, abortion and the generation of persistently infected calves, which can develop fatal "Mucosal Disease".

Within BVDV two major genotypes exist which are classified as different species within the genus pestivirus: BVDV Type 1 and Type 2. Both Type 1 and Type 2 can cause acute and persistent infection, but members of the Type 2 were described to cause more severe symptoms in acutely infected animals.

With regard to virulence, however, there is in general not that much difference between Type 1 and Type 2.

The pestivirus genome consists of a single-stranded RNA of positive orientation. The RNA has a length of approximately 12.3 kb and contains one large open reading frame (ORF), which is flanked by non-translated regions (NTR) at both genome ends. The pestiviral ORF is translated into one polyprotein, which is co- and post-translationally processed into 12 mature proteins by viral and cellular proteases. The first protein of the pestiviral ORF is Npro (N-terminal protease). Npro is a non-structural autoprotease that cleaves itself off the rest of the ORF encoded polyprotein, and thereby creates its own C-terminus and also the correct N-terminus for the first structural protein in the ORF, the C (core) protein. The C protein in the ORF is followed by the other structural proteins: $E^{rns}$, E1, E2 in that order. Together, the capsid (C) protein and the three glycosylated envelope proteins ($E^{rns}$, E1, E2) make up the pestiviral virion.

The E2-protein is the immuno-dominant protein of Pestiviruses, containing the major neutralizing epitopes. It is therefore the target of the protective immune response elicited in the host after natural infection or following immunization with live or killed vaccines. The E2 protein forms, together with the $E^{rns}$ and E1 protein, the surface proteins protruding from the viral envelope. In this context, the E1-E2 heterodimer is a very important structure for virus assembly and attachment.

Currently, both live attenuated and killed vaccines are commercially available. Live attenuated vaccines have the advantage that they mimic a natural infection, and they have to be administered in most cases only once. They however can have some virulence, which makes them sometimes less suitable for the vaccination of young animals and especially of pregnant animals or animals in contact to pregnant animals. Killed vaccines are accepted as safe, but usually they have to be administered twice, in order to provide an adequate level of protection. In addition, efficacy is in many cases reduced and often restricted to closely related BVDV strains and types.

Live attenuated vaccines are currently frequently used vaccines. For BVDV, live attenuated vaccines for the protection of animals against BVDV Type 1 and Type 2 infection are available. It is clear that, if only for commercial reasons, such vaccines should preferably be given as a combination vaccine, i.e. at the same time and, even more convenient, mixed in the same syringe. It was found however that, whereas BVDV Type 1 or 2 live attenuated vaccines when given as single vaccination provide excellent protection, a combination vaccine provides a significantly lower level of protection. Single live attenuated vaccines provide so-called sterile immunity (=no virus excretion and no viraemia), whereas a combination vaccine does not provide sterile immunity. Even a vaccination regime in which the vaccination with one type and the vaccination with another type are separated in time for 4 weeks shows this disadvantageous effect. The mechanism for this effect is unknown.

Thus, there is a need for improvement of BVDV combination vaccines.

It is an objective of the present invention to provide improved BVDV vaccines, in which the disadvantages of mutual negative effects of e.g. BVDV Types 1 and 2 as seen in a combination vaccine are less severe or even absent.

In this respect, one embodiment of the present invention relates to a Bovine Viral Diarrhoea virus (BVDV) belonging to a first Type, characterised in that it is a chimeric BVDV, carrying an E2 gene of a second BVDV Type.

It was surprisingly found now, that if a BVDV of a certain Type is used in a vaccine for the protection of a susceptible ruminant against BVD wherein that BVDV additionally carries an E2 gene of a second BVDV Type, the mutual negative effects mentioned above are less severe or even absent.

Therefore, one embodiment of the present invention relates to Bovine Viral Diarrhoea virus (BVDV) belonging to a first Type, characterised in that it is a chimeric BVDV, additionally carrying an E2 gene of a second BVDV Type.

It was also surprisingly found now, that if a BVD virus of a certain first Type is used in a combination vaccine for the protection of a susceptible ruminant against BVDV, together with a chimeric BVDV having a backbone of the same first Type, however carrying an E2 gene of a second BVDV Type, instead of an E2 of the first BVDV Type, the mutual negative effects are also less severe or even absent.

Such a chimeric virus can then be combined for vaccination purposes with a BVD virus having the same backbone as the chimeric virus however carrying the original E2 as normally present in that virus. Merely as an example, the chimeric BVDV can be a Type 1 virus of which the E2 gene has been replaced with the E2 gene of a Type 2 virus, and it can be combined with a BVDV Type 1 virus with its own (=Type 1) E2 gene.

The backbone of BVDV, the part of the virus that is not exchanged, for the understanding of the invention is basically formed by the replication machinery; the non-structural genes. However, merely in order to elucidate the concept of backbone; in those cases where only the E2 gene is replaced, one could consider the viral backbone to be the whole viral genome except for E2. In those cases where e.g. in addition to the E2 gene, another structural gene such as e.g. the E1 gene is replaced, one could consider the viral backbone to be the whole viral genome except for E2 and E1.

As said above, it is in principle possible to leave the original E2-gene of the chimeric virus in place. The chimeric virus would then encode e.g. both a BVDV Type 1 E2 and a BVDV Type 2 E2.

Preferably, however, there would be a replacement of the original E2 gene by an E2-gene encoding a different E2 Type.

The reason is, that a combination vaccine comprising 1) a chimeric BVD virus according to the invention with a replacement of the original E2 gene by an E2-gene encoding a different E2 Type, and 2) a BVD virus having the same backbone and its original E2 Type would guarantee that (provided that equal amounts of the viruses are administered) the amount of E2 of each Type produced would roughly be comparable.

In case of a chimeric BVDV comprising both the original E2 gene and a second E2 gene of another type, it might be less easy to ensure equal expression levels of both E2 genes. This is because in such a virus one of the two E2-genes would be inserted in the virus outside its natural context.

When BVDV according to the invention is used in a vaccine, it is clear that the virus should behave attenuated, compared to wild type virus.

Therefore, preferably a BVDV according to the invention is a live attenuated virus.

Another embodiment of the invention relates to vaccines for the protection of susceptible ruminants against BVDV, wherein such vaccines comprise a Bovine Viral Diarrhoea virus (BVDV) belonging to a first Type, characterised in that it is a chimeric BVDV, additionally carrying an E2 gene of a second Type and a pharmaceutically acceptable carrier. Such chimeric virus would then encode e.g. both a Type 1 E2 and a Type 2 E2, as explained above.

As said above, a BVDV of a certain type wherein the E2 of that type is replaced by another type, would for reasons given above be very suitable for use in a combination vaccine.

Therefore, another embodiment relates to a combination vaccine for the protection of susceptible ruminants against BVDV, which vaccine comprises a first BVDV belonging to a first Type and carrying a BVDV E2 gene of that first Type, a second BVDV also belonging to a first Type, however characterised in that of this second BVDV the BVDV E2 gene belonging to the first Type is replaced by a BVDV E2 gene belonging to a second Type, and a pharmaceutically acceptable carrier.

As mentioned above, the E2 protein forms, together with the $E^{rns}$ and E1 protein, the surface proteins protruding from the viral envelope. In this context, the E1-E2 heterodimer is a very important structure for virus assembly and attachment.

Thus, a preferred form of a combination vaccine relates to a combination vaccine according to the invention wherein, in addition, in the second BVDV the BVDV E1 gene belonging to said first Type is replaced by a BVDV E1 gene belonging to a second Type.

In principle, this system can be used for all related Pestiviruses, also for the atypical ones like the HoBi-Virus group, which is now also referred to as the future BVDV-3 Type.

However, BVDV Type 1 and Type 2 are the common types causing disease. Therefore, preferably the backbone of the virus belongs to Type 1 type and the E2 gene belongs to the Type 2 type or vice versa.

Thus a more preferred form of this embodiment relates to a combination vaccine according to the invention wherein the backbone of the first and second BVD virus belongs to Type 1 and the BVDV E2 gene of the second BVD virus belongs to Type 2.

An equally more preferred form of this embodiment relates to a combination vaccine according to the invention wherein the backbone of the first and second BVD virus belongs to Type 2 and the BVDV E2 gene of the second BVD virus belongs to Type 1.

The first BVDV, the one described above as "belonging to a first Type and carrying a BVDV E2 gene of that first Type" would usually be a standard BVD virus of Type 1 or 2 without alterations in E2. This first BVDV would preferably be a live attenuated virus.

The second BVDV, described above as "also belonging to a first Type, however characterised in that of this second BVDV the BVDV E2 gene belonging to the first Type is replaced by a BVDV E2 gene belonging to a second Type" would usually be a virus of Type 1 or 2, now however carrying a BVDV E2 gene of a Type 2 or 1, respectively. This second BVDV would also preferably be a live attenuated virus.

Pharmaceutically acceptable carriers are well-known in the art. Merely as an example; such a carrier can be sterile water or a buffer solution such as PBS.

Merely for reasons of ease of producing a vaccine, it would be practical if both the first and the second BVDV have an identical backbone. As already indicated above, by using one and the same backbone for both viruses, one could simply add the same amount of both viruses having highly comparable replication efficacy and properties to the combination vaccine and by doing so safely assume that both viruses have the same level of attenuation and replication capacity, that roughly the same amount of cells would be infected with each of the viruses and that both the E2 protein of Type 1 and the E2 protein of Type 2 would be expressed in roughly the same amount of protein and replicating a comparable amount of RNA molecules in vitro and in vivo.

Thus, a preferred form of this embodiment relates to a combination vaccine according to the invention wherein the first BVDV and the second BVDV have the same backbone.

As mentioned above, BVDV strains for use in a vaccine must be attenuated. Several of such attenuated BVDV vaccine strains have been described and several attenuated BVDV vaccine strains are commercially available. Most promising vaccine types comprise a deletion in the $N^{pro}$ gene and/or in the $E^{rns}$ gene, and are of a cytopathic biotype. Pestivirus vaccines on the basis of such deletions have i.a. been described in PCT-Patent Application WO 99/64604, US-Patent Application US 2004/0146854, European Patent Application EP 1104676, European Patent Application EP 1013757, European Patent Application EP 1440149, European Patent EP 1751276 and by Mayer, D., et al., Vaccine 22:317-328 (2004).

Thus, a more preferred form of this embodiment relates to a combination vaccine according to the invention wherein that first BVDV and/or said second BVDV comprise a deletion in the $N^{pro}$ gene and/or in the $E^{rns}$ gene.

BVDV is only one of several agents causing disease in ruminants. In practice, ruminants are vaccinated against a number of virus or micro-organism pathogenic to ruminants. Therefore it is highly attractive, both for practical and economical reasons, to combine the combination vaccine according to the invention with an additional antigen of a virus or micro-organism pathogenic to ruminants, an antibody against said antigen or genetic information encoding an immunogenic polypeptide of said virus or micro-organism.

Thus, an even more preferred form of this embodiment relates to a combination vaccine according to the invention, wherein that vaccine comprises an additional antigen of a virus or micro-organism pathogenic to ruminants, an antibody against said antigen or genetic information encoding an immunogenic polypeptide of said virus or micro-organism.

The most common pathogenic viruses and micro-organisms pathogenic for ruminants are Bovine Rotavirus, Bovine Herpesvirus, Parainfluenza Type 3 virus, Bovine Paramyxovirus, Bluetongue virus, Foot and Mouth Disease virus, *Pasteurella haemolytica* and Bovine Respiratory Syncytial Virus.

Therefore, a still even more preferred form of the invention relates to a combination vaccine according to the invention, wherein the virus or micro-organism pathogenic to ruminants is selected from the group of Bovine Rotavirus, Bovine Herpesvirus, Parainfluenza Type 3 virus, Bovine Paramyxovirus, Bluetongue virus, Foot and Mouth Disease virus, *Pasteurella haemolytica* and Bovine Respiratory Syncytial Virus.

The additional antigen of a virus or a micro-organism can be the whole virus or micro-organism (in a live attenuated form or in an inactivated form) or an immunogenic polypeptide or another immunogenic part of that virus or micro-organism such as e.g. a (lipo-)polysaccharide, capable of inducing a protective immune response.

Vaccines comprising live attenuated viruses must be stored at low temperature, or they have to be in a freeze-dried form. Freeze-dried vaccines can be kept under moderate cooling conditions or even at room temperature. Often, the vaccine is mixed with stabilizers, e.g. to protect degradation-prone proteins from being degraded, to enhance the shelf-life of the vaccine, or to improve freeze-drying efficiency. Useful stabilizers are i.a. SPGA, carbohydrates e.g. sorbitol, mannitol, trehalose, starch, sucrose, dextran or glucose, proteins such as albumin or casein or degradation products thereof, and buffers, such as alkali metal phosphates.

Therefore, preferably, the combination vaccine according to the invention is in a freeze-dried form.

In addition, the vaccine may be suspended in a physiologically acceptable diluent. Such buffers can e.g. be sterile water, a buffer and the like.

It goes without saying, that diluents and compounds for emulsifying or stabilizing viruses are also embodied in the present invention.

A suitable amount of each of the BVDV in the combination vaccine according to the invention would be between $10^2$ and $10^8$ TCID$_{50}$ depending on the level of attenuation of the virus used. The literature cited above and the knowledge in the art would give the skilled person ample guidance to determine the amount of virus needed. In case the vaccine strains used are based upon existing, commercially available (cp) BVDV strains comprising an attenuating deletion, such as a deletion in the N$^{pro}$ gene and/or in the E$^{rns}$ gene, the manufacturer's instructions would suffice to know how much virus should be used.

As a rule of thumb, for e.g. (cp) BVDV strains carrying a mutation in the N$^{pro}$ and/or E$^{rns}$ gene, an amount of $10^5$ TCID$_{50}$ would be a very suitable amount of virus.

Combination vaccines according to the invention can be administered via the known administration routes. Such routes comprise i.a. intranasal, intramuscular, intravenous, intradermal, oral and subcutaneous routes.

Still another embodiment of the invention relates to BVDV for use as a medicament Again another embodiment of the invention relates to BVDV for use in the treatment of Bovine Viral Diarrhoea.

Still another embodiment of the present invention relates to methods for the manufacture of a vaccine according to the invention, wherein the method comprises the step of mixing a BVDV belonging to a first Type, wherein that BVDV is a chimeric BVDV, additionally carrying an E2 gene of a second BVDV Type, and a pharmaceutically acceptable carrier.

Finally, another embodiment of the present invention relates to methods for the manufacture of a combination vaccine according to the invention, wherein the method comprises the step of mixing a first BVDV belonging to a first Type, a second BVDV also belonging to that first Type and carrying a BVDV E2 gene of that first Type, and a pharmaceutically acceptable carrier.

LEGEND TO THE FIGURES

Figure 1:
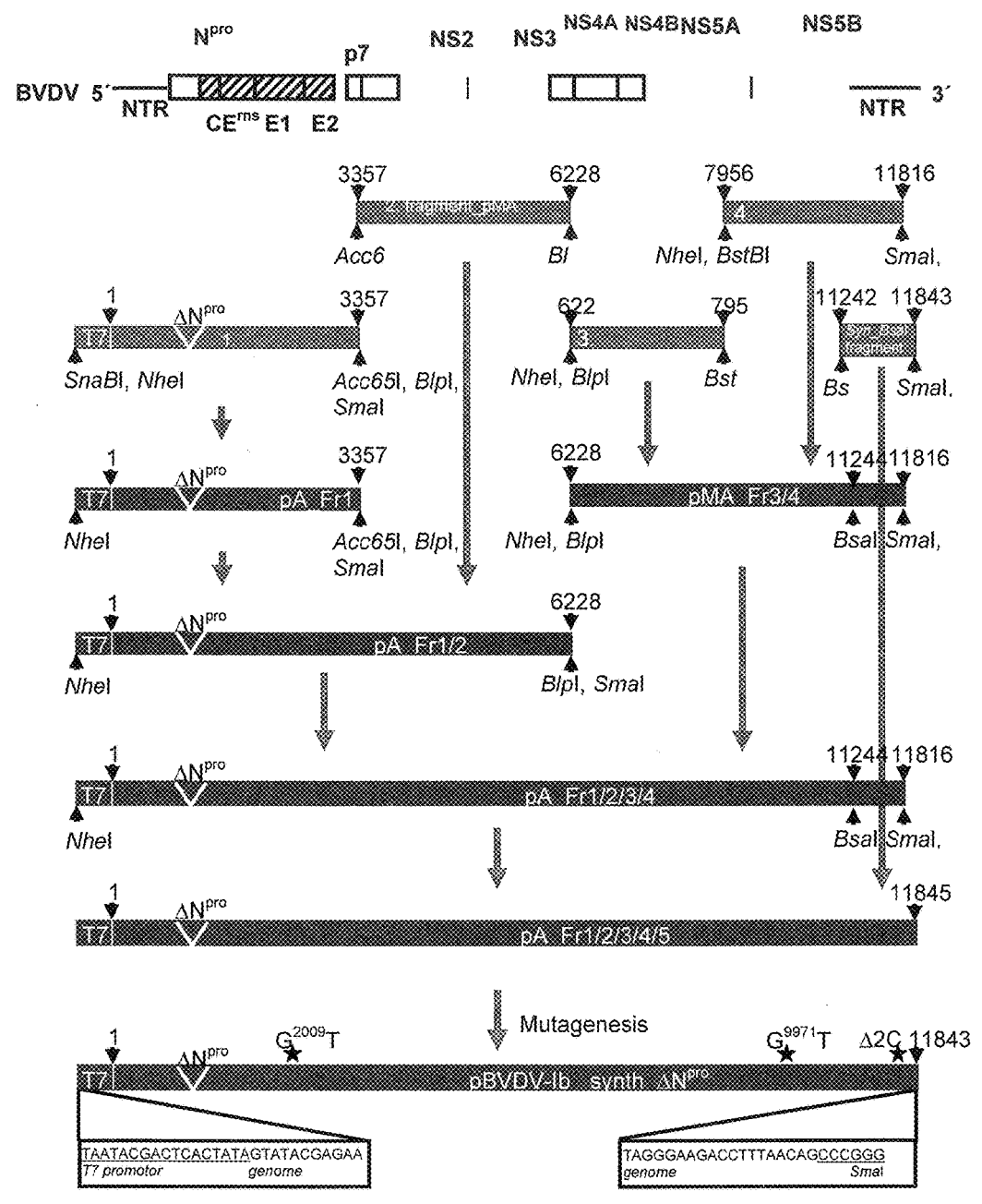

FIG. 1: Schematic representation of the BVDV genome and the construction of pBVDV-1b_synth_ΔN$^{pro}$.

FIG. 2: Schematic representation of the BVDV genome and the construction of full-length pBVDV-1 b_synth.

Figure 3:
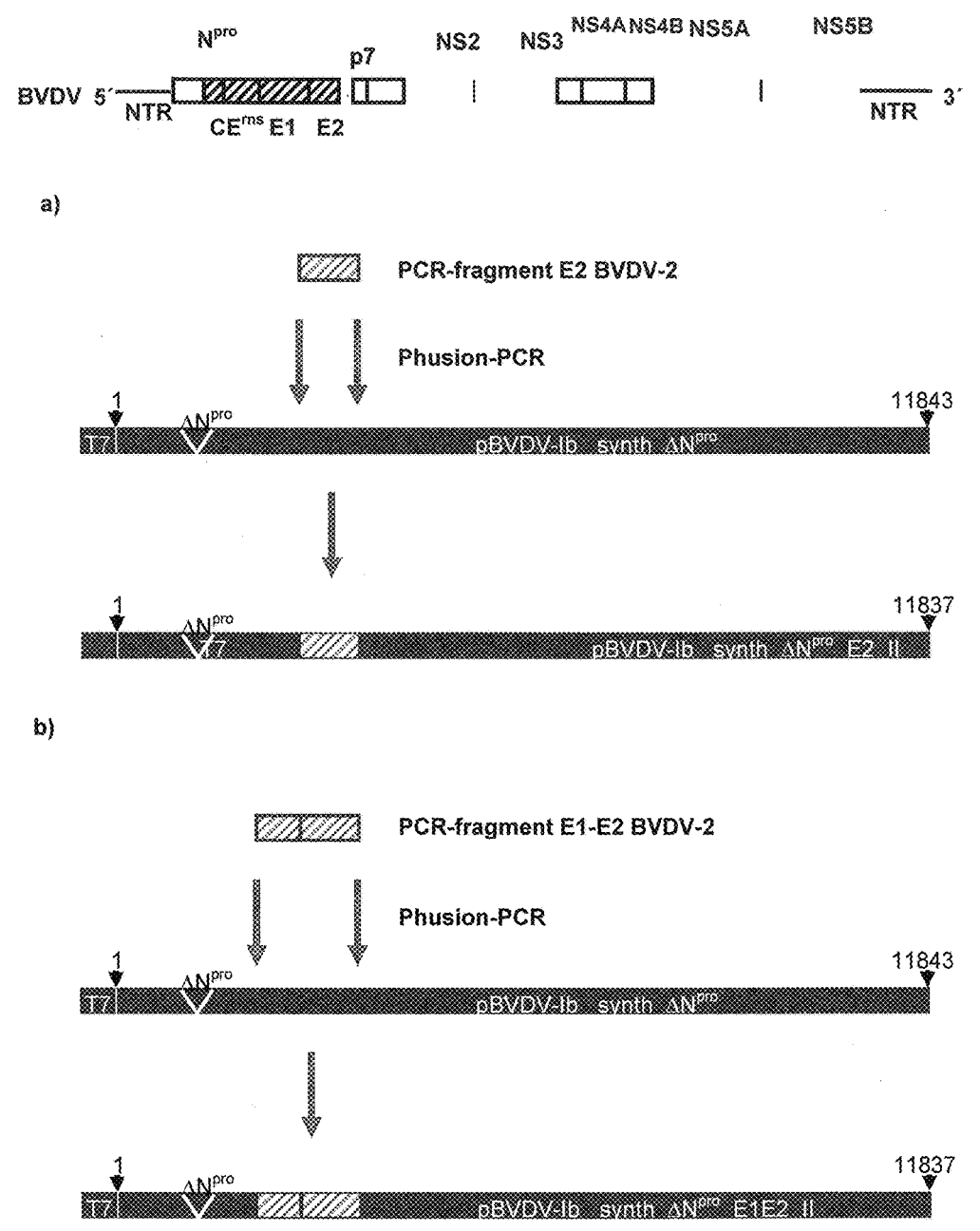

FIG. 3: Schematic representation of the BVDV genome and the construction of chimeric E2/E1E2 constructs on the basis of pBVDV-1b_synth.

Figure 4:
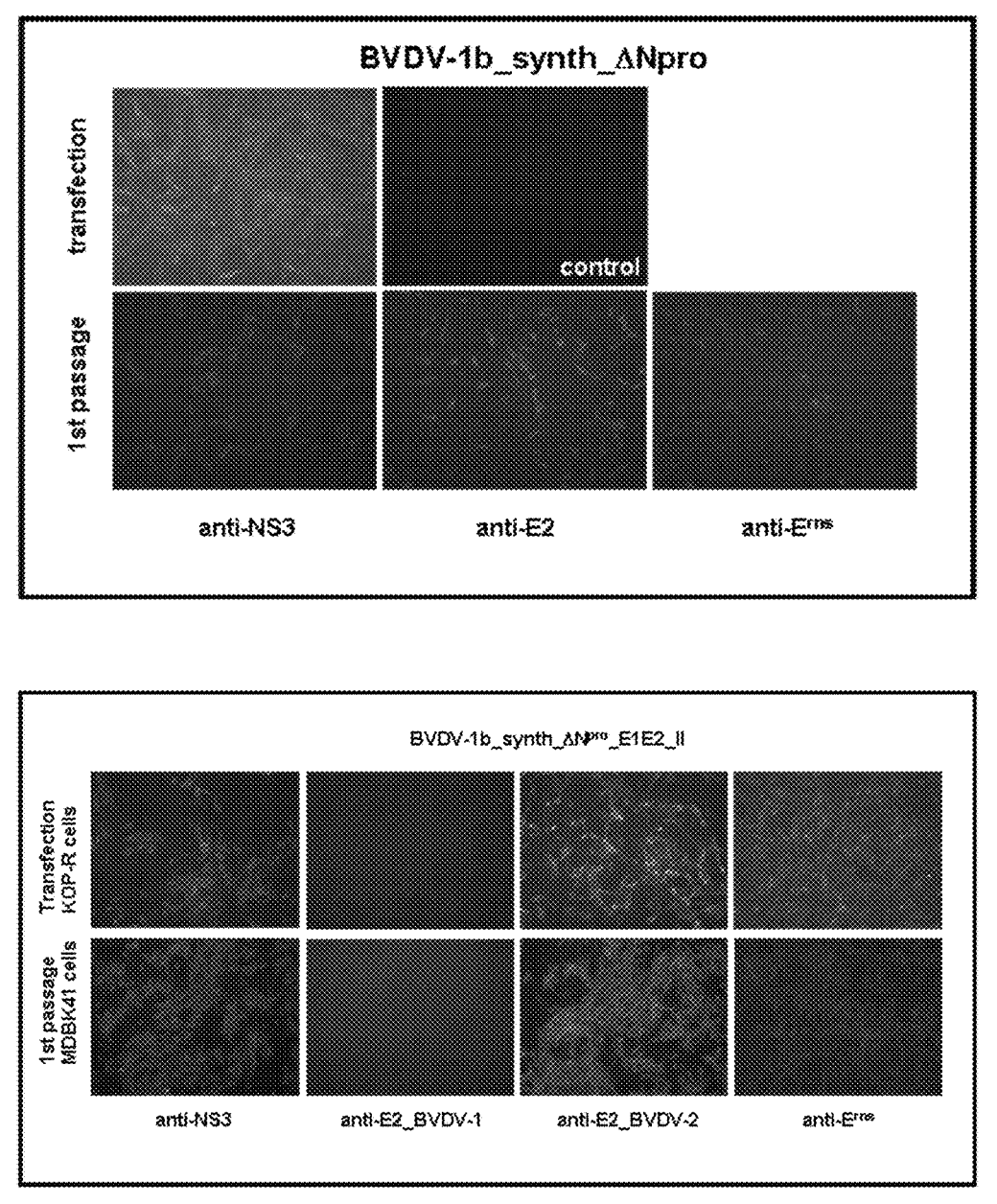

FIG. 4: IF analysis of bovine cells (KOP-R) transfected with in vitro-transcribed RNA of the synthetic cDNA constructs.

Figure 5:
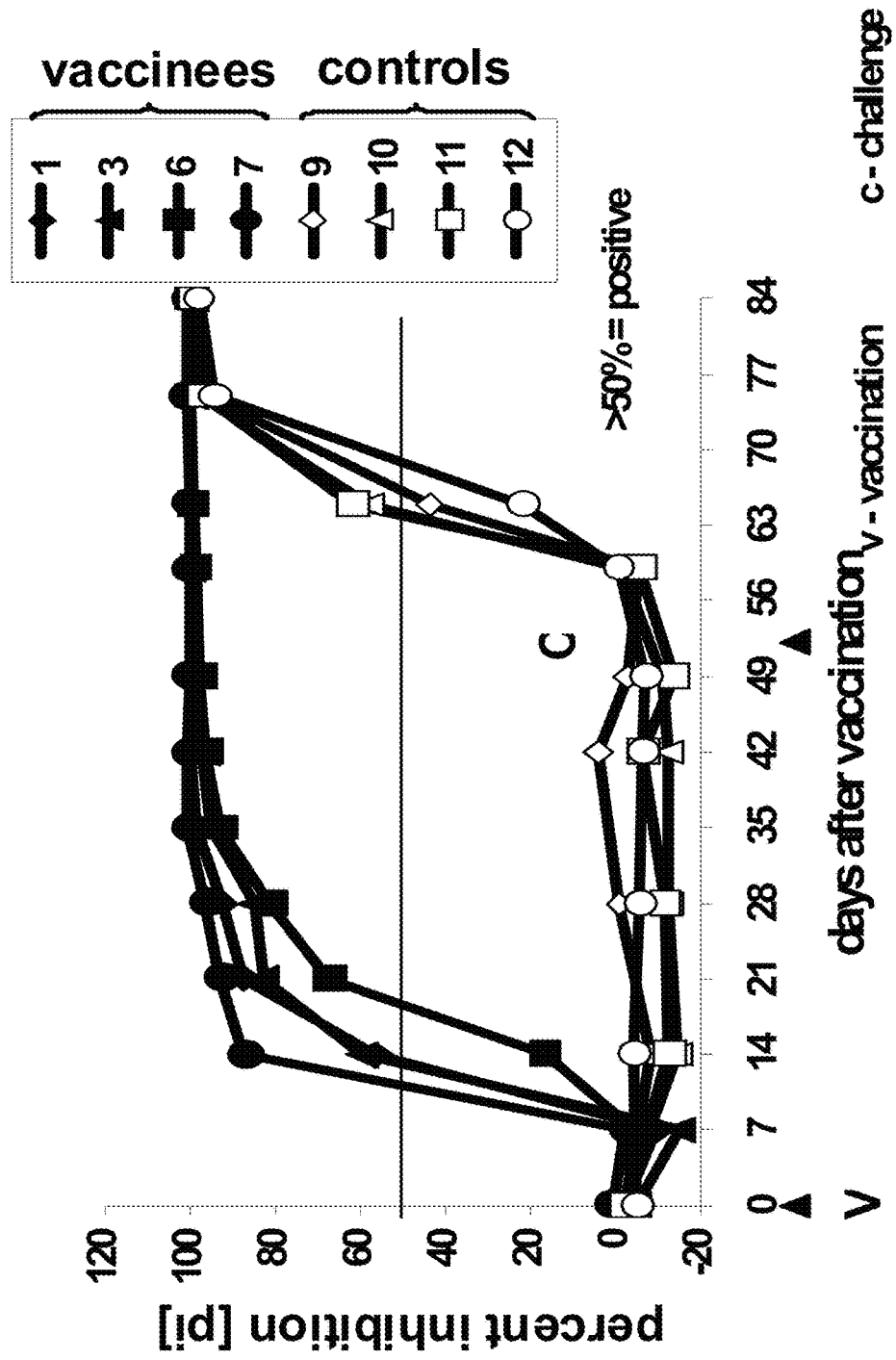

FIG. 5: BVDV NS3 blocking ELISA

Figure 6:
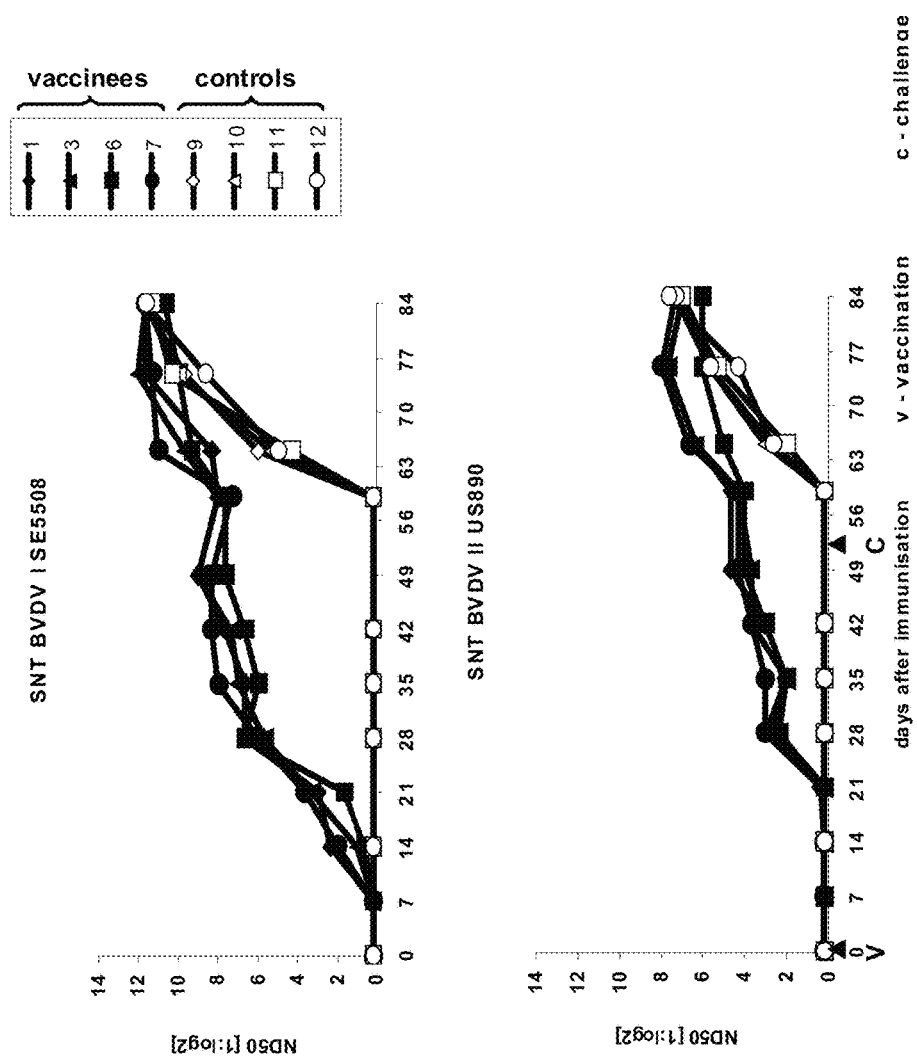

FIG. 6: BVDV neutralization assay

FIG. 7: Scheme of the experimental design of animal trial 1 on the CP7 ΔNpro vaccination-challenge trial.

FIG. 8: Scheme of the experimental design of the animal trial on NCP7 ΔNpro trial—transplacental infection.

FIG. 9: Time scale, sampling periods and experimental design of animal trial 1 on the cp7ΔNpro/v890FLΔNpro/v890FLΔC vaccination-challenge trial.

FIG. 10: Time scale, sampling periods and experimental design of animal trial 2 on the cp7ΔNpro/v890FLΔNpro sequential vaccination-challenge trial.

FIG. 11: Time scale, sampling periods and experimental design of animal trial 3 on the BVDV-1/2 chimera (cp7ΔNpro_E2CS8644) vaccination-challenge trial.

REFERENCES

Meyers, G., Tautz, N., Becher, P., Thiel, H. J., und Kümmerer, B. M. (1996). Recovery of cytopathogenic and noncytopathogenic bovine viral diarrhoea viruses from cDNA constructs. J. Virol. 70, 8606-8613.

Geiser, M., Cebe, R., Drewello, D. and Schmitz, R. (2001). Integration of PCR fragments at any specific site within cloning vectors without the use of restriction enzymes and DNA ligase. Biotechniques 31, 88-90, 92.

Wolfmeyer, A., Wolf, G., Beer, M., Strube, W., Hehnen, H. R., Schmeer, N. and Kaaden, O. R. (1997). Genomic (5'UTR) and serological differences among German BVDV field isolates. Arch. Virol. 142, 2049-2057.

EXAMPLES

Example 1

Construction of Synthetic BVDV Clones
1. Introduction

A BVDV type 1b virus was synthesized completely based on a synthetic construct. The sequence is similar to the published sequence of the BVDV 1b prototype strain "CP7" and the published full-length plasmid sequence pA/BVDV CP7 (Meyers et al. 1996; Genbank Accession no U63479), however, essential changes and adaptations were included. Furthermore, two recombinant viruses were constructed on the basis of the synthetic clone: a Npro deleted virus as well as a chimeric virus expressing BVDV type 2 E2 instead of the original BVDV 1b E2.

Data for Construction of pBVDV-1b_synth_$\Delta N^{pro}$

Plasmids were amplified in *Escherichia coli* DH10B™ cells (Invitrogen). Plasmid DNA was purified by using Qiagen Plasmid Mini or Midi Kit. Restriction enzyme digestion and cloning procedures were performed according to standard protocols. Sequencing was carried out using a Big Dye® Terminator v1.1 Cycle sequencing Kit (Applied Biosystems). Nucleotide sequences were read with an automatic sequencer (3130 Genetic Analyzer, Applied Biosystems) and analyzed using the Genetics Computer Group software version 11.1 (Accelrys Inc., San Diego, USA). Site-directed mutagenesis was done by using QuickChange II XL Site-Directed Mutagenesis Kit (Stratagene) and Phusion PCR (Geiser et al., 2001), respectively.

Primers for mutagenesis were synthesized by MWG-Biotech and biomers.net GmbH and are listed in table 1.

pBVDV-1b_synth_$\Delta N^{pro}$ was constituted from five plasmids harboring the synthetic sequence fragments (1. fragment_pGA15, 2. fragment_pMA, 3. fragment_pMK, 4. fragment_pMA, Syn_BsaI_fragment_pMK_RQ) which were all in vitro synthesized by the GENEART AG (Regensburg, Germany). By using this synthetic fragments and their unique restriction sites, one full-length plasmid construct was generated. Restriction enzyme digestions and cloning procedures were performed according to standard protocols. The synthetic sequence fragments are described below. The construction of the infectious cDNA clone pBVDV-1b_synth_$\Delta N^{pro}$ is shown in FIG. 1. Location of restriction sites and nucleotide positions corresponding to the BVDV genome (most similar strain is CP7) are indicated by arrows.

1. fragment_pGA15 contains nucleotides 1 to 3357 (Acc65I site) corresponding to BVDV1b$\Delta N^{pro}$. At the 5' NTR the sequence of the T7 promoter was added to enable in vitro transcription as well as SnaBI and NheI sites. A second Acc65I$^{2007}$ site was removed by a silent mutation of GGTACC to ATATCC.

2. fragment_pMA contains nucleotides 3357 to 6228 (BlpI site).

3. fragment-pMK contains nucleotides 6288 to 7956 (BstBI site).

4. fragment_pMA contains nucleotides 7956 to 11816 (SmaI site). A second BstBI$^{7965}$ site was removed by a silent mutation of TTCGAA to TTCGAG.

Syn_BsaI fragment_pMK_RQ contains nucleotides 11244 to 11816 (SmaI site) with the 3' NTR and a SmaI site for linearization of plasmid DNA prior in vitro transcription.

For generation of pBVDV-1b_synth_$\Delta N^{pro}$ a carrier plasmid was digested with SmaI and dephosphorylated and eluted after agarose gel electrophoresis.

1.Fragment_pMA was digested with SnaBI and SmaI, and the virus specific fragment was isolated. Both fragments were ligated resulting in plasmid pAFr1. Afterwards, plasmid pA_Fr1 was linearised by using Acc65I and BlpI and the Acc65I$^{3357}$-BlpI$^{6228}$ fragment isolated from plasmid.

TABLE 1

Nucleotide sequence of primers used for site directed mutagenesis and Phusion-PCR

| Primer | Sequence 5' → 3'[a] | Genomic region |
|---|---|---|
| Mut_2009_F | ACAGGGGCGCAAGG<u>A</u>T<u>A</u>TCCAGACTGCAAACCC | 2430-2462[b] (+sense) |
| Mut_2009_R | GGGTTTGCAGTCTGG<u>A</u>T<u>A</u>TCCTTGCGCCCCTGT | 2462-2430[b] (-sense) |
| Ph_10375_F | cggaagcaggaattaggttggaaaaattacc | 10363-10393[b] (+sense) |
| Ph_10551R | CGTCACTGTAGGTGTGTCTTAGGC | 10551-10528[b] (-sense) |
| CP711973F | Gcaagaactagcccagtcacg | 11973-11993[b] (+sense) |
| CP7_3C_R | <u>CTAGTGGATCCCCCGGGCTGTTAAAGGTCTTCCC</u> | 11843-11824[c] (-sense) |
| Ph_E2CS_F | GCTCATAACAGGGGCGCAAGGG*ATTCCCTGAATGCAAAGAGGG* | 2423-2444[b] (+sense) |
| Ph_E2CS_R | cacctgccccatactggacacctatagctacttgctctgac | 3585-3567[b] (-sense) |
| Ph_E1CS_F | catggtttggggcatatgca<u>gcaagtccatactgtgatgtg</u> | 1840-1859[b] (+sense) |

[a]nucleotides, different from BVDV-1 CP7 sequence (Accession No. U63479) are underlined; sequences of BVDV-2 CS8644 (unpublished) are in italics
[b]nucleotide position corresponding to BVDV CP7 sequence
[c]nucleotide position corresponding to pBVDV-1b_synth_$\Delta N^{pro}$ 2.fragment_pMA was inserted resulting in plasmid pA_Fr1/2. Plasmid pMA_Fr3/4 was generated by ligation of NheI and BstBI$^{7956}$ digested plasmid 4.fragment_pMA, and a BlpI$^{6628}$/BstBI$^{7956}$ fragment was isolated from plasmid 3.fragment_pMK. This plasmid was subsequently digested with BlpI$^{6628}$/SmaI$^{11816}$, and the resulting BlpI$^{6628}$/SmaI$^{11816}$ fragment was ligated into BlpI$^{6628}$/SmaI plasmid pA_Fr1/2. Within the resulting plasmid pAFr1/2/3/4 the BsaI fragment was substituted with the BsaI fragment isolated from plasmid Syn_BsaI fragment_pMK_RQ leading to the full-length cDNA construct pAFr1/2/3/4/5. For the generation of infectious virus progeny two mutations, G$^{2011}$T and G$^{9948}$T were inserted by site directed mutagenesis resulting in the infectious full length cDNA construct pBVDV-1b_synth_ΔN$^{pro}$.

Construction of pBVDV-1b_synth

The BVDV full-length cDNA clone pBVDV-1b_synth was constructed on the basis of pBVDV-1b_synth_ΔN$^{pro}$ by insertion of an Acc65I/$^{3793}$ XhoI$^{208}$-fragment of the plasmid pBVDV-1b_deltaNS (nucleotides 1-4597), into pBVDV-1b_synth_ΔN$^{pro}$ (FIG. 2). To this end the plasmid pBVDV-1b_synth_ΔN$^{pro}$ was digested with Acc65I$^{3357}$ and XhoI$^{231}$ and ligated with the Acc65I/$^{3793}$ XhoI$^{208}$-fragment of pBVDV-1 bdeltaNS.

Construction of pBVDV-1b_synth_ΔN$^{pro}$_BVDV-2_E2

The BVDV full-length cDNA clone pBVDV-1b_synth_ΔN$^{pro}$_BVDV-2_E2 is a BVDV-1b/BVDV-2 chimeric construct which was generated by substitution of the genomic region encoding for E2 of pBVDV-1b_synth_ΔN$^{pro}$ (nucleotides 2009-3130) with the genomic region encoding for E2 of BVDV-2 (isolate CS8644; Wolfmeyer et al., 1997).

The chimeric pestivirus clone pBVDV-1b_synth_ΔN$^{pro}$_BVDV-2_E2 was constructed by Phusion PCR (FIG. 3a). In a first step an E2-megaprimer was generated by PCR using primers Ph-E2CS_F and Ph_E2CS_R. As template for PCR plasmid pGEM_E1E2_CS, which contains the E1 and E2 encoding genomic region of BVDV-2 isolate CS8644, was utilized. In a second PCR, the Phusion-PCR, E2-CS8644 sequences were introduced into the full-length plasmid pBVDV-1b_synth_ΔN$^{pro}$ by using the E2-megaprimer and pBVDV-1b_synth_ΔN$^{pro}$ as template.

Construction of pBVDV-1b_synth_ΔN$^{pro}$_BVDV-2_E1-E2

The BVDV full-length cDNA clone pBVDV-1b_synth_ΔN$^{pro}$_BVDV-2_E1-E2 is a BVDV-1b/BVDV-2 chimeric construct which was generated by substitution of the genomic region encoding for E1 and E2 of pBVDV-1b_synth_ΔN$^{pro}$ (nucleotides 1424-3130) with the genomic region encoding for E1 and E2 of BVDV-2 (isolate CS8644; Wolfmeyer et al., 1997).

The chimeric pestivirus clone pBVDV-1b_synth_ΔN$^{pro}$_BVDV-2_E1-E2 was constructed by Phusion PCR (FIG. 3b). In a first step an E1-E2-megaprimer was generated by PCR using primers Ph-E1CS_F and Ph_E2CS_R. As template for PCR the plasmid pGEM_E1E2_CS was used. By Phusion-PCR, E1 and E2-CS8644 sequences were introduced into the full-length plasmid pBVDV-1b_synth_ΔN$^{pro}$ by using the E1-E2-megaprimer and pBVDV-1b_synth_ΔN$^{pro}$ as template.

FIG. 1:

Schematic representation of the BVDV genome and the construction of pBVDV-1b_synth_ΔN$^{pro}$. The viral genome was synthesized in five fragments (Geneart AG), 1.fragment_pGA15, 2.fragment_pMA, 3.fragment_pMK, 4.fragment_pMA, and Syn_BsaI_fragment_pMK_RQ (light blue boxes). Plasmid 1.fragment_pGA15 harbours the N$^{pro}$ deletion (ΔN$^{pro}$). At the 5'-NTR the sequence of the T7 promotor was added to enable in vitro transcription. For plasmid linearization a SmaI restriction site was introduce at the 3' NTR. Location of restriction sites and nucleotide positions corresponding to the BVDV 1bΔN$^{pro}$ genome (most similarity to BVDV strain CP7) are indicated by short black arrows. The full-length cDNA construct pBVDV-1b_synth_ΔN$^{pro}$ was constituted exclusively from the five synthesized fragments as demonstrated by the grey arrows and dark blue boxes. No virus RNAs or cDNA were used for the construction.

In vitro mutagenesis steps during the construction are indicated by stars. Shaded boxes represent the BVDV structural protein region. Lines at the left and the right ends indicate non-translated regions. N$^{pro}$, autoprotease; C, capsid protein; E$^{rns}$, E1, E2, envelope proteins; p7, NS2 to NS5, nonstructural proteins.

FIG. 2:

Schematic representation of the BVDV genome and the construction of full-length pBVDV-1b_synth. Shaded boxes represent the BVDV structural protein region. Lines at the left and the right ends indicate non-translated regions. N$^{pro}$, autoprotease; C, capsid protein; E$^{rns}$, E1, E2, envelope proteins; p7, NS2 to NS5, nonstructural proteins. The full-length cDNA construct pBVDV-1b_synth was constructed by insertion of an Acc65I/$^{3793}$ XhoI$^{208}$-fragment of the plasmid pBVDV-1bdeltaNS which contains parts of the sequence of a BVDV-1b fragment (nucleotides 1-4597) including the Npro encoding genomic region, into pBVDV-1b_synth_ΔN$^{pro}$.

FIG. 3:

Schematic representation of the BVDV genome and the construction of chimeric E2/E1E2 constructs on the basis of pBVDV-1b_synth. Shaded boxes represent the BVDV structural protein region. Lines at the left and the right ends indicate non-translated regions. N$^{pro}$,autoprotease; C, capsid protein; E$^{rns}$, E1, E2, envelope proteins; p7, NS2 to NS5, nonstructural proteins. The chimeric pestivirus clones pBVDV-1b_synth_ΔN$^{pro}$_BVDV-2_E2 (a) and pBVDV-1b_synth_ΔN$^{pro}$_BVDV-2_E1E2 (b) were constructed by using the full-length cDNA clone pBVDV-1b_synth_ΔN$^{pro}$. Genomic region encoding for E2 of pBVDV-1b_synth_ΔN$^{pro}$ (nucleotides 2009-3130) and E1 and E2 of pBVDV-1b_synth_ΔN$^{pro}$ (nucleotides 1424-3130), respectively, were substituted by the respective genomic region of BVDV-2 isolate CS8644 (Wolfmeyer et al., 1997) by Phusion PCR by using Primers Ph_E1_F and Ph_E2_R. As template for PCR plasmid pGEM_E1E2_CS was used, which contains the E1 and E2 encoding genomic region of BVDV-2 isolate CS8644.

FIG. 4:

IF-analysis of bovine cells (KOP-R) transfected with in vitro-transcribed RNA of the synthetic cDNA constructs. For the detection of BVDV proteins the monoclonal antibodies C16 (anti-NS3, Institute for Virology, TiHo Hannover), WB215 (anti-E2 BVDV-1, CVL, Weybridge), BA-2 (VMRD), and WB210 (anti-E$^{rns}$, CVL, Weybridge) were used.

Cell Culture and Virus Propagation

Cells and viruses were grown in Dulbecco's Modified Eagle Medium (DMEM) supplemented with 10% BVDV-free foetal bovine serum at 37° C. in a humidified atmosphere containing 5% CO$_2$. pBVDV-1b_synth_ΔN$^{pro}$ was propagated on original MDBK cells or interferon incompetent MDBK cells (Rie728; CCLV) provided by Gunther Keil, FLI, Insel Riems. Virus titres were determined by end point titrations. Cells seeded in microtitration plates were infected with 10-fold serial dilutions of clarified supernatants. The titres expressed in $TCID_{50}$ per milliliter were obtained by immunofluorescence staining of the cultures with the monoclonal antibody (mAb) C16 directed against the pestiviral protein NS3 (kindly provided by the Institute of Virology, TiHo, Hannover, Germany) and an Alexa Fluor®488 conjugated $F(ab')_2$ fragment of goat anti-mouse IgG (Molecular Probes, Leiden, The Netherlands). Virus preparations were tested for the absence of $N^{pro}$ and mycoplasma.

In Vitro Transcription and RNA Transfection

In vitro transcription of the synthetic full-length cDNA constructs was performed using the T7 RiboMax Large-Scale RNA Production System (Promega) according to the manufacturer's instructions after linearising the plasmid with SmaI. The amount of RNA was estimated by ethidium bromide staining after agarose gel electrophoresis. For RNA transfection, bovine cells were detached using a trypsin solution, washed twice with phosphate buffered saline without Ca++/Mg++ (PBS−) and mixed with 1-5 µg of in vitro sythesized RNA. Electroporation was done by using the GenePulser transfection unit (Biorad) (two pulses at 850 V, 25 µF and 156 ω).

Immunofluorescence Staining

Cell cultures were fixed with 4% paraformaldehyde (PFA) and permeabilised with 0.01% digitonin (IF staining of NS3) or fixed/permeabilised with 80% acetone ($E^{rns}$, E2), and incubated with the appropriate working dilution of the respective antibodies for 30 min. After one washing step with PBS−, cells were incubated with the $Alexa^{488}$-conjugated secondary antibody for 30 min and finally washed. IF was analysed by using a fluorescence microscope (Olympus).

Example 2

CP7 $\Delta N^{pro}$ Vaccination-Challenge Trial

The scheme of the CP7 $\Delta N^{pro}$ experimental design of animal trial 1 is represented in FIG. 7.

BVDV naïve calves (n=4 per group) were vaccinated or mock-vaccinated and 52 days later, a challenge infection with BVDV type Ib strain SE5508 (Wolfmeyer et al., 1997) was performed.

Vaccination: single application of 6.7 $\log_{10}$ $TCID_{50}$ BVDV CP7 $\Delta N^{pro}$ i.m. (5 ml)

Mock vaccination: uninfected cell culture supernatant i.m. (5 ml)

Challenge infection: 6.5 $\log_{10}$ $TCID_{50}$ BVDV SE5508 (Ib) i.n., nebuliser, 2 ml Results White blood cells were purified from EDTA-blood after alkaline lyses of erythrocytes. 100 µl of swab fluid or $3\times10^6$ leukocytes were inoculated on bovine cells in 4 parallels. After 5-6 days of co-cultivation virus replication was verified by indirect immunofluorescence testing (IIFT). One further blind passage of the supernatants was performed (6 d→IIFT).

In 1 out of 4 calves cell bound viremia was detected. Low amounts of CP7 $\Delta N^{pro}$ could be re-isolated on day 4 after vaccination after the first cell culture passage.

No nasal excretion of vaccine virus was recorded.

After challenge infection, no nasal shedding of BVDV SE5508 was detected in the vaccinated animals. All vaccinees were completely protected against viremia, and no challenge virus was re-isolated from purified white blood cells ("sterile immunity").

In contrast, all control calves exhibited nasal BVDV excretion for 6-8 days, as well as cell-bound viremia during 6-8 days.

After vaccination all animals immunised with CP7 $\Delta N^{pro}$ displayed a moderate drop of the leukocyte counts with recovery to pre-vaccination values until 7 days after inoculation.

After challenge infection no significant decrease of white blood cells was observed in the immunised calves. The mean blood cell counts remained within the physiological range.

In the control animals, a marked leukopaenia was observed with an onset at 3 days after challenge. The average leukocyte counts stayed low for more than 2 weeks.

In comparison to the pre-vaccination temperatures, only a faint elevation of the rectal body temperatures was recorded after vaccination.

After challenge infection, the immunised animals showed no alterations of the temperature curves. In regard of a temperature response, the animals were clearly protected from clinical BVD.

In all control calves, a moderate raise of the temperatures occurred at 3 days after inoculation.

After more than one week, body temperatures returned to the pre-challenge levels.

All animals were monitored for altered general conditions and respiratory or gastrointestinal symptoms typical for BVDV.

Over the whole observation period day (4 weeks prior to immunisation until 12 weeks thereafter), mainly in the vaccinated animals, alternating mild respiratory symptoms such as nasal discharge and sporadic coughing were observed. After vaccination, no adverse clinical reactions occurred. In the vaccines, no exacerbation of the pre-vaccination scores was observed.

After challenge infection, the immunised animals showed no clinical symptoms. In the control calves, mild respiratory symptoms were recorded and feed uptake was reduced for 1-2 days. The animals showed neither gastrointestinal disorders nor mucosal lesions.

Serological responses of the animals were monitored using a BVDV ELISA (NS3-blocking; FIG. 5) as well as BVDV type I and type II specific neutralization assay (FIG. 6).

All animals inoculated with CP7 $\Delta N^{pro}$ seroconverted for BVDV NS3-specific antibodies until 3 weeks after vaccination, as tested by the Ceditest BVDV ELISA (Cedi diagnostics). The control calves remained negative until 2-3 weeks after challenge infection (FIG. 5).

After vaccination, all animals developed BVDV type I neutralising antibodies at moderate titres (FIG. 6). After challenge infection (c), the immunised animals showed no pronounced booster of the neutralising antibody titres. The mock vaccinated animals were tested negative until 2 weeks after challenge infection with BVDV type I strain SE5508. BVDV type II (strain US980) specific neutralising antibodies at low titres were also induced after vaccination. Neutralising antibody titres were comparable to the values of the control animals at 3 weeks after inoculation with the BVDV type I field strain SE5508.

Example 3

NCP7 ΔNpro Trial—Transplacental Infection

The scheme of the experimental design of this animal trial is presented in FIG. 8.

BVDV naïve heifers (n=4 per group) were intravenously and intranasally inoculated with NCP7ΔN$^{pro}$ or with the parental virus NCP7 between d 71 and 79 of pregnancy (=first trimester).

application of 6.0 log$_{10}$ TCID$_{50}$ BVDV NCP7: 10 ml i.v.+5 ml i.n.

6.1 log$_{10}$ TCID$_{50}$ BVDV NCP7 ΔN$^{pro}$: 10 ml i.v.+5 ml i.n.

Results

Until 2 weeks after virus inoculation, the heifers were monitored for viremia and nasal virus shedding. 100 µl of swab fluid or 3×10$^6$ purified blood leukocytes were inoculated on bovine cells in 4 parallels. After 5-6 days of co-culture virus replication was verified by indirect immunofluorescence testing (IIFT). One additional blind passage of the supernatants was performed (6 d→IIFT).

Short and low titered virus shedding was observed in all NCP7-animals but could be verified only for 1 out of 4 heifers after inoculation of the N$^{pro}$ deletion mutant. Viremia could be detected in all infected animals with a more than 2 days longer average duration for the parental virus.

In both inoculated groups a marked decrease of the leukocyte counts was observed after infection. Blood leukocyte values declined as early as one day after inoculation of NCP7ΔN$^{pro}$ with recovery to pre-infection values after 7 days. Following infection with the parental virus strain CP7 a more protracted course of leukocyte reduction was evident with onset at 4 days p.i. and regression at 8 d p.i. The maximal reduction values between both groups were comparable.

Compared to the body temperature means prior to infection, only a faint elevation of the rectal body temperatures was recorded for the NCP7 group but remained within a physiological range.

The animals were monitored for altered general conditions and respiratory or gastrointestinal symptoms typical for BVDV. In all animals mild nasal and ocular discharge as well as coughing was sporadically observed over the whole period. After infection no adverse reactions occurred and in both groups only a mild increase of respiratory disorder was observed.

Antibody development was monitored with a BVDV NS3-blocking ELISA. All inoculated animals seroconverted for NS3-specific antibodies until 2-3 weeks after vaccination, as tested by the Ceditest BVDV ELISA (Cedi Diagnostics).

Performance of Gravidity:

NCP7: animal 5: abortion on day 71 p.i.

fetus mummified, virus isolation from all organ and blood samples negative but positive from bone marrow lavage (¼ replicates)

NCP7ΔN$^{pro}$: animal 4: abortion on day 46 p.i.

advanced mazeration, dead for 2-3 weeks, isolation from all organ and blood samples negative The heifers were sacrificed approximately at 12 weeks after BVDV infection. Gross necropsy did not reveal any fetopathogenic effects. Development, size, and weight of the fetuses were inconspicuous.

Virus isolation in cell culture was performed from 0.3 g of organ material (shock frozen, ground with sea sand) followed by 2 consecutive passages of the supernatants in case of first negative results.

| Virus isolation from maternal and fetal tissues NCP7 | | | |
|---|---|---|---|
|  | animal 3 | animal 2 | animal 1 |
| tonsil (mother) | 4x – | 4x – | 4x – |
| uterus (mother) | 4x – | 4x – | 4x – |
| cotyledone | 4x – | 4x – | 4x – |
| amnion | +++/1x++/2x+ | +++/2x+/– | +/(+)/–/ – |
| skin | 4x +++ | 4x +++ | 4x +++ |
| thyreoidea | 4x +++ | 4x +++ | 4x +++ |
| thymus | 4x +++ | 4x +++ | 4x +++ |
| liver | 4x +++ | 4x +++ | 4x +++ |
| kidney | 4x +++ | 4x +++ | 4x +++ |
| intestine (ileum) | 4x +++ | 4x +++ | 4x +++ |
| parotis | 4x +++ | 4x +++ | 4x +++ |
| tonsil | 4x +++ | 4x +++ | 4x +++ |
| lung | 4x +++ | 4x +++ | 4x +++ |
| spleen | 4x +++ | 4x +++ | 4x +++ |
| cerebellum | 4x +++ | 4x +++ | 4x +++ |
| lymphnode | 4x +++ | 4x +++ | 4x +++ |
| lavage of bon | 4x +++ | 4x +++ | 4x +++ |
| purified leuko | 4x +++ | 4x +++ | 4x +++ |
| allantoic fluid | 2x +++/++/+ | 4x +++ | 4x +++ |
| serum | 2x ++/2x+ | 4x +++ | 4x +++ |

4 replicates
Graduation of fluorescence intensity:
+: plaques
++: non-infected spots
+++: layer completely infected
NCP7 ΔN$^{pro}$: all samples negative Virus isolation was conducted on KOP-R cells, interferon-incompetent MDBK cells, and on the highly susceptible MDBK-clone 6.

Furthermore, 1 g of fetal tissue material was homogenised and cultured in flasks on interferon-incompetent MDBK cells and on MDBK-clone 6 cells. The cultures, as well as 2 additional passages, were stained negative for BVDV in immunofluorescence analyses.

Fetal tissues were also subjected to quantitative real-time RT-PCR (qRT-PCR) analyses. At present, we tested leukocytes, lung and kidney.

Genome copies were extrapolated to 1.0 g of tissue material, 1 ml whole blood or 1 ml bone marrow lavage.

The parental BVDV strain NCP7 as well as the N$^{pro}$ deletion mutant crossed the placenta and were able to establish infection in all fetuses. However, no infectious NCP7ΔN$^{pro}$ virus was re-isolated from a large panel of fetal organs. In addition, no virus genomes could be detected in purified blood leukocytes of the NCP7ΔN$^{pro}$ fetuses. In comparison with the BVDV NCP7 RNA loads for, the copy numbers of NCP7ΔN$^{pro}$ were 5,000-fold (lungs) to 20,000-fold (kidney) reduced.

Example 4

Comparison of Vaccines/Vaccination Strategies

1$^{st}$ Animal Trial: Vaccination Challenge Trial v890FLΔC, cp7ΔN$^{pro}$; v890FLΔN$^{pro}$ and a combination of both N$^{pro}$ mutants in a single application were used to vaccinate groups of cattle (2 different vaccination schemes).

2$^{nd}$ Animal Trial: Vaccination Challenge Trial cp7ΔN$^{pro}$ and v890FLΔN$^{pro}$ where administered as a sequential vaccine (1$^{st}$ shot: cp7ΔN$^{pro}$/2$^{nd}$ shot: v890FLΔN$^{pro}$)

3$^{rd}$ Animal Trial: Vaccination Challenge Trial cp7ΔN$^{pro}$_E2CS8644, a chimera composed of cp7ΔN$^{pro}$ as backbone with the cp7 E2 replaced by the E2 coding region of the BVDV-2 strain CS8644 was used as vaccine candidate, either solely or in combination with cp7ΔN$^{pro}$ in one single application.

Challenge Strain

For all three trials a virulent German field isolate, BVDV-2 strain HI916, which causes reproducible and clear clinical signs of disease as determined in a previous trial was used.

Further Indication to all Labels/Legends of Below Given Schemes and Diagrams (if Mutants are not Explicitly Named):

| BVDV-2 or 890 | stands for | v890FL |
|---|---|---|
| BVDV-1 | stands for | cp7ΔN$^{pro}$ |
| ΔN | means | ΔN$^{pro}$ |

Design of the cp7ΔN$^{pro}$/v890FLΔN$^{pro}$/v890FLΔC Vaccination-Challenge Trial Animal trial 1 time scale, sampling periods and experimental design is represented in FIG. 9

TABLE 2

Outline of the animal groups used in the cp7ΔNpro/v890FLΔNpro/v890FLΔC vaccination-challenge trial

| 5 BVDV-2ΔC | 5 controls | 5 BVDV-1ΔNpro | 5 BVDV-2ΔNpro & BVDV-1ΔNpro | 5 BVDV-2ΔNpro |
|---|---|---|---|---|
| 1$^{st}$ 1.02 × 10$^6$ TCID50/animal | unvaccinated | 9.28 × 10$^5$ TCID50/animal | 1.26 × 10$^6$ TCID50/animal | 9.28 × 10$^5$ TCID50/animal |
| 2$^{nd}$ 6.32 × 10$^5$ TCID50/animal i.m. | i.m. | i.m. | i.m. | i.m. | challenge infection
2.25 × 10$^6$ TCID50/animal i.n. (nebulizer)
heterologous BVDV-2 HI916
(assessed as effective and virulent challenge strain in previous trial)

Animals:

25 BVDV naïve calves (n=5 per group) were vaccinated according to the protocol and 60 days later, a challenge infection with BVDV-2 strain HI916 (German field isolate, established as challenge strain in a previous animal trial) was carried out.

Vaccination:
double application of BVDV v890FLΔC: 1$^{st}$ shot: 1.02× 10$^6$/2$^{nd}$ shot: 6.32×10$^5$ TCID50 (2 ml i.m.)
single application of 9.28×10$^5$ TCID50 BVDV cp7ΔN$^{pro}$ (2 ml i.m.)
single application of 9.28×10$^5$ TCID50 BVDV v890FLΔN$^{pro}$ (2 ml i.m.)
single application of 1.26×10$^6$ TCID50 BVDV cp7ΔN$^{pro}$ & v890FLΔN$^{pro}$ (2 ml i.m.)

Challenge Infection:
2.25×10$^6$ TCID50 BVDV-2 HI916 intranasally—using a nebulizer Sampling Periods:
daily for 10 days after vaccination (v890FLΔC group: for 8 days after 1st vaccination, no sampling after 2$^{nd}$ vaccination/no sampling of the control group)
all groups for 14 d after challenge infection Results I
I.I Vaccination:
v890FLΔC (Vaccination d 0 and d 25)
1$^{st}$ Vaccination (d 0):
 Clinical Signs and Blood Picture:
  animals showed neither adverse reactions nor a temperature rise or clinical signs of disease.
  no leucopenia could be observed.
 Virus Isolation:
  neither shedding via nasal excretions nor pseudovirion viremia was detectable by virus isolation→therefore, the group was not sampled following second vaccination
 Serology:
  developed only a marginal rise in inhibition levels and remained negative until booster vaccination the applied NS3-specific blocking ELISA (Prionics)
  neutralising antibody titres against all three strains tested (BVDV-1: SE5508/BVDV-2: 890 and HI916) were not detectable after the first vaccination
2$^{nd}$ Vaccination (d 25):
 not sampled for vi and blood picture
 Serology:
  showed a clear boost in antibody development being ELISA positive as soon as 7 days after their second vaccination
  stayed at basal to non detectable neutralising titre levels until challenge infection—very low to nonexistent—even against the parental BVDV-2 890 strain
cp7ΔN$^{pro}$ (Vaccination d 25)
 Clinical Signs and Blood Picture:
  one animal showed a little elevation in temperature for one (day 28)
  some clinical reaction post vaccination; animals had slightly elevated mean clinical score values for 2 days (day 28 and day 35) due to mild respiratory symptoms
  short and monophasic decline in leukocyte counts (up to 20% reduction day 29/30)
  thrombocyte counts also slightly decreased paralleling leukocyte counts
 Virus Isolation:
  no nasal virus shedding and very limited vaccine virus viremia (3 animals, 2 days)
 Serology:
  positive in the NS3 blocking ELISA from day 14 p. vacc.
  neutralising antibody titres were found in all immunised groups as soon as 14 days after vaccination:
   BVDV-1 SE5508: highest titres of all groups
   BVDV-2 HI916: medium titres
   BVDV-2 890: similar values and trends as against HI916
v890FLΔN$^{pro}$ (Vaccination d 25)
 Clinical Signs and Blood Picture:
  one animal showed a little elevation in temperature for two days (day 31, day 32).
  no raised clinical scores
  short and monophasic decline in their leukocyte counts (up to 20% reduction day 30)
  thrombocyte counts also slightly decreased paralleling leukocyte counts
 Virus Isolation:
  vaccine virus was detected in the nasal swab sample from one immunised animal on one single day (day 32, after blind passage)—very limited vaccine virus viremia 2 animals, 3 to 4 days Serology:
  positive in the NS3 blocking ELISA from day 14 p. vacc.
  neutralising antibody titres as soon as 14 days after vaccination
    BVDV-1 SE5508: stayed basal in their titres
    BVDV-2 HI916: highest titres
    BVDV-2 890: similar values and trends as against H916
cp7ΔN$^{pro}$ & V890FLΔN$^{pro}$ (Vaccination d 25)
  Clinical Signs and Blood Picture:
  no temperature rise after vaccination
  no raised clinical scores
  short and monophasic decline in their leukocyte counts (max 28%)
  thrombocyte counts also slightly decreased paralleling leukocyte counts
  Virus Isolation:
  no nasal virus shedding and very limited vaccine virus viremia (3 animals, 1 to 2 days)
  Serology:
  positive in a NS3 blocking ELISA from day 14 p. vacc.
  neutralising antibody titres were found as soon as 14 days after vaccination
    BVDV-1 SE5508: highest titres
    BVDV-2 HI916: high titres (lower than solely BVDV-2Npro application group)
    BVDV-2 890: similar values and trends
Controls: (Unvaccinated)
  stayed seronegative during the vaccination period stayed basal in their titres
I.II Challenge Infection (Day 60)
Controls:
  Clinical Signs and Blood Picture:
  biphasic rise in body temperatures: a slight one at day 3 and a pronounced one at days 8 and 9 p. chall. with maximum mean group values of up to 41° C.
  showed typical and clear signs of clinical disease: distinct rise in clinical scores peaking at days 8 to 10: marked respiratory symptoms (coughing and mucopurulent nasal discharge), depression with reduced appetite, 2 animals had a watery diarrhoea for 2 to 3 days
  developed a severe leukopaenia: bi- to triphasic decrease (days 3, 7 and 13 p. chall.) in leukocyte counts with maximum levels of 48% reduction at day 7 p. chall.
  thrombocyte counts were not as heavily affected as expected: mean reduction to a maximum of 35% at day 3 p. chall.
  counts notably increased after acute infection in the controls (to mean values of 195%), corresponding to severity of infection and disease
  Virus Isolation:
  challenge virus was detectable in the nasal swab samples of all control animals from day 61 till day 71—long and distinct challenge virus viremia in the control group for up to 11 days (day 62-day 73)
  Serology:
  all control animals scored positive in the NS3 blocking ELISA from day 14 p. chall. on
  detectable neutralising titres from day 14 on against all three strains, higher titres against BVDV-2 strains
BVDV-2ΔC
  Clinical Signs and Blood Picture:
  elevation in body temperature at day 7 but stayed in the physiological range
  clinical effects of the challenge infection were clearly reduced compared to the controls
  only a single decline of the leukocyte counts: maximal decrease of about 12% on day 4 p. chall; quickly recovered to pre-infection counts (day 7 p. chall.)
  thrombocyte counts: a single less marked decrease.
  Virus Isolation:
  duration and levels of nasal virus shedding markedly reduced: all animals shed on 1 to 4 days—challenge virus viremia: also clearly reduced in time and amount BVDV-2ΔC: 4 animals, 1 day
  Serology:
  NS3 antibodies were slightly boostered; mean blocking values of 100% were reached at day 89
  boost in neutralising antibodies titres, detectable after 7 resp.14 days post challenge and peaking at day 14 to day 28 p. chall.
    BVDV-1 SE5508 increased, but mean values peaked at a markedly lower level than against BVDV-2 strains
    BVDV-2 strain 890: titres after 7 days; at the term of the study end titres were very similar in all groups
    BVDV-2 strain HI916: titres remained slightly lower than against 890 strain
BVDV-1ΔN$^{pro}$
  Clinical Signs and Blood Picture:
  elevation in body temperature at day 7 p. chall. up to 40° C.
  clinical effects of the challenge infection were clearly reduced; moderate respiratory symptoms noticed
  only a single decline of leukocyte counts (maximal decrease of about 12% 4 p. chall.); animals quickly recovered to pre-infection counts (day 7 p. chall.)
  thrombocyte counts: no marked decrease; after acute infection notably increased (175%)
  Virus Isolation:
  nasal virus shedding: duration (day 62-day 68) and levels markedly reduced: 4 animals, 1 to 3 days—challenge virus viremia: clear reduction in time (day 63-day 68) and amount: all animals, 1 to 5 days;
  Serology:
  NS3 antibodies (blocking ELISA (Prionics)): slightly boostered; mean blocking values of 100% reached at day 89
  boost effect on neutralising antibodies titres peaking at day 14 to day 28 p. chall.
    BVDV-1 SE5508: maximum titres reached 14 days post challenge
    BVDV-2 890: maximum titres 14 days post challenge; at the term of the study end titres were very similar in the groups
    BVDV-2 HI916: maximum titres 14 days post challenge; remained slightly lower than against 890 strain
BVDV-2ΔN$^{pro}$
  Clinical Signs and Blood Picture:
  no elevation in body temperature
  no clinical effects
  no decrease in leukocyte blood counts
  thrombocyte counts: a single decrease up to 20% on day 4 post challenge.
  Virus Isolation:
  neither shedding of challenge virus nor challenge virus viremia
  Serology:
  NS3 antibodies (blocking ELISA (Prionics)): slightly boostered; mean blocking values of 100% reached at day 89
  boost effect on neutralising antibodies titres peaking at day 14 to day 28 p. chall.

BVDV-1 SE5508: increased, but mean values peaked at a markedly lower level than groups receiving BVDV-1.

BVDV-2 890: maximum titres 14 days post challenge; at the term of the study end titres were very similar in the groups BVDV-2 HI916: maximum titres 14 days post challenge; similar to titres against BVDV-2 890

BVDV-1ΔN$^{pro}$+BVDV-2ΔN$^{pro}$

Clinical Signs and Blood Picture:

single elevation in body temperature at day 7 (39.8° C.)

clinical effects of the challenge infection were clearly reduced; no rise of clinical scores single decline of the leukocyte counts (maximal decrease of 24% at day 10 p. chall.), reduced leukocyte counts persisted till the end of the trial (day 89—mean reduction of 20 thrombocyte counts: single decrease of 25% on day 5 post challenge; increased after day Virus Isolation:

nasal virus shedding: duration and levels markedly reduced: 2 animals, 1 to 2 days—challenge virus viremia: clear reduction in time and amount: 2 animals, 1 to 3 days Serology:

NS3 antibodies (blocking ELISA (Prionics)): slightly boostered; mean blocking values of 100% reached at day 89 boost effect on neutralising antibodies titres peaking at day 14 to day 28 p. chall.

BVDV-1 SE5508: increased, but mean values peaked at a markedly lower level than groups receiving BVDV-1.

BVDV-2 890: maximum titres 14 days post challenge; at the term of the study end titres were very similar in the groups BVDV-2 HI916: maximum titres 14 days post challenge; similar to titres against BVDV-2 890

In General:

No clinical effects like bloody diarrhoea, petechia or haematomas on injection/injury sites could be observed in this trial.

The conducted neutralising assays in this study showed that titres of BVDV-2 exposed animals against BVDV-2 strains were lower than those of the BVDV-1 vaccinated animals against the used BVDV-1 strain.

Due to widely differing results of the NS3-specific ELISA and the neutralisation assay for the BVDV-2ΔC-immunised group, we sequenced the region of the replicon encoding the E2 protein. The E2 protein is the major immunogen of BVDV and the predominant inducer of neutralising antibodies. We found one nucleotide change compared to the corresponding sequence of the parental full-length cDNA clone. It was located at nucleotide position 2736 referred to the full-length cDNA and leads to an amino acid change from Leucine to histidine.

Conclusions:

All BVDV vaccine candidates tested for safety and efficacy markedly reduced the outcome of the heterologous BVDV-2 challenge infection in cattle while showing graduated protective effects with regards to clinical symptoms, nasal virus shedding and viremia. The v890FLΔN$^{pro}$ mutant provided complete protection leading to a "sterile immunity" against the highly virulent BVDV-2 challenge in all immunized animals. A vaccine comprising both the cp7ΔN$^{pro}$ and the v890FLΔN$^{pro}$ strain did not provide sterile immunity against the same highly virulent BVDV-2 challenge.

Design of the cp7ΔN$^{pro}$/v890FLΔN$^{pro}$ sequential vaccination-challenge trial Animal trial 2 time scale, sampling periods and experimental design is represented in FIG. 10.

TABLE 3

Outline of the animal groups used in the cp7ΔNpro/v890FLΔNpro sequential vaccination-challenge trial

| 5<br>BVDV-1ΔNpro<br>+<br>BVDV-2ΔNpro | 4<br>controls |
|---|---|
| 1$^{st}$ (BVDV-1 Δ Npro)<br>1.12 × 10$^6$ TCID50/animal<br>2$^{nd}$ (BVDV-2 Δ Npro)<br>1.26 × 10$^5$ TCID50/animal<br>i.m. | unvaccinated<br>i.m. | challenge infection
1.66 × 10$^5$ TCID50/animal i.n.
(nebulizer)
heterologous BVDV-2 HI916
(assessed as effective and virulent challenge strain in previous trial)

Animals:

9 BVDV naïve calves (n=5 vaccinated/n=4 unvaccinated control group) were vaccinated sequentially; 2 shots with an interval of 28 days according to the protocol and 28 days after the 2$^{nd}$ vaccination a challenge infection with BVDV-2 strain HI1916 (German field isolate, established as challenge strain in a previous animal trial) was carried out.

Vaccination:

1$^{st}$ shot CP7 ΔNpro: 1.12×10$^6$ TCID50/animal (2 ml i.m.)

2$^{nd}$ shot v890FLΔNpro: 1.26×10$^5$ TCID50/animal (2 ml i.m.)

Challenge Infection:

1.66×10$^5$ TCID50 BVDV-2 HI916 intranasally—using a nebulizer

Results II

II.I Vaccination (Day −56 and Day −28)

cp7ΔN$^{pro}$/v890FLΔN$^{pro}$

1$^{st}$ Vaccination d −56 (cp7ΔN$^{pro}$)

Clinical Signs and Blood Picture:

body temperatures of the animals stayed in the physiological range no adverse clinical reactions occurred; slight clinical (mainly respiratory) symptoms 7-8 days after vaccination led to an elevated score but were unlikely associated with vaccination, as alternating mild respiratory symptoms such as nasal discharge and sporadic coughing were observed during the whole period of monitoring in both groups leukocyte counts (weekly intervals): declined during first 4 weeks thrombocyte counts (weekly intervals): stayed unaffected Serology:

positive in the applied antibody ELISA (IDEXX) from 14 d post vaccination neutralising antibodies detectable in the neutralisation assays from day 14 p. vacc.

BVDV-1 SE5508: clear rise from day 14 p.vacc.

BVDV-2 890: low to medium titres detectable on day 14

BVDV-2 HI916: titres basal to non detectable until second vaccination

2$^{nd}$ Vaccination d −28 (v890FLΔN$^{pro}$)

Clinical Signs and Blood Picture:
  body temperatures of the animals stayed in the physiological range
  no rise in the clinical score
  leukocyte counts (weekly intervals): a very slight decline (around 5%) displayed in a biphasic spiked curve between day −26 and −21
  thrombocyte counts (weekly intervals): stayed unaffected Virus Isolation:
  no vaccine virus shedding nor vaccine virus viremia could be observed Serology:
  clear booster effect in the antibody ELISA from 7 d post second vaccination
  neutralising antibodies clearly boostered from day 7 p. 2$^{nd}$ vacc.
    BVDV-1 SE5508: clear boost; maximum titres already reached before challenge infection
    BVDV-2 890: clear boost
    BVDV-2 HI916: boost to detectable, but very low titres Controls:
  Serology:
    stayed seronegative throughout the sampling period (ELISA and NAs)

In General:
  General decline in leukocyte counts in both groups over the first 4 weeks of the vaccination period could be indication of elevated counts at the start of the trial caused e.g. by a foregone (general) infection.

II.II Challenge Infection (Day 0):

Controls:
  Clinical Signs and Blood Picture:
    biphasic rise in their body temperatures: a very slight one at day 2 and 4 (remaining in the physiological range) and a moderate one at days 8 and 9 p. chall. with maximum mean group values of 39.7° C.
    showed typical and clear signs of clinical disease: rise in clinical scores peaking at days 8 to 10: respiratory symptoms (coughing and mucopurulent nasal discharge), slight depression with reduced appetite
    developed a clear leukopaenia: bi- to triphasic decrease (days 3, 7 and 11 p. chall.) of leukocyte counts with maximum levels of 45% reduction at day 7 p. chall.
    thrombocyte counts were not as heavily affected as expected: biphasic drop (day 7 and 11) with a mean reduction to a maximum of 40-50% afterwards counts notably increased till day 21 following acute infection in the controls (to mean values of 270%)
  Virus Isolation:
    challenge virus was detectable in the nasal swab samples of all control animals from day 1 till day 10—long and distinct challenge virus viremia in the control group for up to 10 days (day 2-day 11)
  Serology:
    animals scored positive in the antibody ELISA from day 14 p. chall. on
    detectable neutralising titres from day 14 on against all three strains, higher titres against BVDV-2 strains
      BVDV-1 SE5508: positive, but low titres till the end of trial
      BVDV-2 890: clear boost
      BVDV-2 HI916: clear boost CP7ΔNpro/v890FLΔNpro
  Clinical Signs and Blood Picture:
    slight elevation in body temperature at day 8 but stayed in the physiological range
    clinical effects of the challenge infection were clearly reduced compared to the controls; infection led not to a rise in the mean clinical scores
    biphasic decline of the leukocyte counts on day 3 and 12: maximal decrease of about 12% on day 3 p. chall; quickly recovered to pre-infection counts after every drop (day 7/resp. day 14 p. chall.)
    thrombocyte counts: two very slight decreases (about 10%) on day 3 and 11 paralleling the leukocyte picture.
  Virus Isolation:
    duration and levels of nasal virus shedding markedly reduced: one animal was vi positive on 2 days (day 3 and 5); challenge virus viremia: also very clearly reduced in time and amount: 2 animals, 1 to 2 days.
  Serology:
    antibodies were clearly boostered, maximum ODs reached 14 days post challenge
    boost in neutralising antibodies titres observable after 7 resp.14 days all peaking at day 28 p. chall., similar titres against all three strains found at the end of the trial
      BVDV-1 SE5508 only slight increase
      BVDV-2 strain 890: boost to similar end titres as the controls
      BVDV-2 strain HI916: clear boost of the only low neutralising antibody titres developed before challenge infection Conclusions:
Neither vaccine virus viremia nor shedding could be observed in this trial. Again no clinical reactions and no fever could be observed in animals after vaccination.

Decreases of leukocyte counts after second vaccination were not pronounced and also leukocyte reduction after challenge infection was not prominent (~12%). Neutralising antibody titers were developed to similar levels as they were in the mixed application of cp7ΔN$^{pro}$/v890FLΔN$^{pro}$. Challenge virus viremia (2 animals 1-2 days) and shedding (1 animal 2 days) could not be completely hindered and were similar as in the group receiving the single mixed application—nevertheless clearly reduced compared to the control group. Sequential vaccination of cp7ΔN$^{pro}$ and v890FLΔN$^{pro}$ did not lead to a sterile immunity in all animals as did the vaccination with v890FLΔN$^{pro}$ mutant alone.

Design of the BVDV-1/2 Chimera (cp7ΔN$^{pro}$_E2CS8644) Vaccination-Challenge Trial Animal trial 3 time scale, sampling periods and experimental design is represented in FIG. 11.

TABLE 4

Outline of the animal groups used in the BVDV-1/2 chimera (cp7ΔNpro_E2CS8644) vaccination-challenge trial

| 5<br>BVDV-1ΔNpro_E2<br>BVDV-2 | 5<br>BVDV-1ΔNpro<br>+<br>BVDV-1ΔNpro_E2<br>BVDV-2 | 4<br>controls |
|---|---|---|
| 9.36 × 10$^5$ TCID50/animal i.m. | 2.04 × 10$^6$ TCID50/animal i.m. | unvaccinated i.m. |
| challenge infection<br>2.95 × 10$^5$ TCID50/animal i.n. (nebulizer)<br>heterologous BVDV-2 HI916<br>(assessed as effective and virulent challenge strain in previous trial) | | |

Animals:
14 BVDV naïve calves (n=5 per vaccinated group/n=4 unvaccinated controls) were vaccinated according to the protocol and 28 days post vaccination, a challenge infection with BVDV-2 strain HI916 (German field isolate, established as challenge strain in a previous animal trial) was carried out.

Vaccination:
group 1: cp7 ΔNpro_E2CS8644: $9.36 \times 10^5$ TCID50/animal (2 ml i.m.)
group 2: cp7 ΔNpro_E2CS8644+cp7ΔNpro: $2.04 \times 10^6$ TCID50/animal (3 ml i.m.)

Challenge Infection:
$1.66 \times 10^5$ TCID50 BVDV-2 HI916 intranasally—using a nebulizer Sampling Periods:
daily for 11 days after vaccination (no sampling of the control group)
all groups for 14 d after challenge infection Results III.I Vaccination (Day −28):
In General:
Serology after Vaccination:
neutralisation assays against the parental strains of the chimera were performed (BVDV-1 cp7 and BVDV-2 CS8644)

cp7 ΔNpro_E2CS8644
Clinical Signs and Blood Picture:
body temperatures of the animals stayed in the physiological range throughout the vaccination period
no adverse clinical reactions occurred; slight clinical (respiratory) symptoms throughout the vaccination period led intermittently to an elevated score (peaks day −25, −15, −11, −10 and −8) but this was unlikely associated with vaccination, as mild respiratory symptoms such as nasal discharge and sporadic coughing alternating in intensity were observed during the whole period of monitoring in both vaccinated groups
leukocyte counts: a slight biphasic decline (around 10% days 3 and 7 post vaccination); on day—19 animals had reached their pre-vaccination levels again
thrombocyte count: there was a constant decrease over the vaccination period—overall 25-30% in both vaccinated groups, declines after vaccination were only minimal (up to 5%)
Virus Isolation:
no vaccine virus shedding could be observed—vaccine virus was isolated from the leukocytes of one animal on one day (d −24)
Serology:
in the applied NS3 blocking ELISA (Prionics) group stayed negative until challenge infection
neutralising antibodies against BVDV-1 (cp7) and BVDV-2 (CS8644)
BVDV-1 cp7: marginally titres detected 3 weeks p.vacc.; stayed low until challenge infection
BVDV-2 CS8644: detected 3 weeks p.vacc.; higher on day 0 cp7 ΔNpro_E2CS8644+cp7ΔNpro
Clinical Signs and Blood Picture:
body temperatures of the animals stayed in the physiological range throughout the vaccination period
no adverse clinical reactions occurred; slight clinical (respiratory) symptoms throughout the vaccination period led intermittently to an elevated score but this was unlikely associated with vaccination, as mild respiratory symptoms such as nasal discharge and sporadic coughing alternating in intensity were observed during the whole period of monitoring in both vaccinated groups
leukocyte counts: slight decline 3 to 7 days post vaccination with a peak at d 7 p.vacc. (around 20%); increased on day −19 but 10% lower than pre-vaccination levels
thrombocyte count: there was a constant decrease over the vaccination period—overall 25-30% in both vaccinated groups, declines after vaccination were not clearly discernable
Virus Isolation:
neither vaccine virus shedding nor vaccine virus viremia could be observed
Serology:
NS3 blocking ELISA (Prionics): marginally positive 3 weeks after immunisation; clearly positive on day of challenge infection
neutralising antibodies against BVDV-1 (cp7) and BVDV-2 (CS8644)
BVDV-1 cp7: detected from day 14 p.vacc., rising till challenge infection
BVDV-2 CS8644: detected 3 weeks p.vacc.; but clearly lower titres as against BVDV-1

Controls:
Serology:
stayed seronegative throughout the sampling period (ELISA and NAs)
In General:
leukocyte counts: there was a decline of about 20% in both vaccinated groups that stayed at a constant level till challenge infection (the counts were set to 100% prior to challenge)

III.II Challenge Infection (Day 0)
In General:
Serology after Challenge Infection:
additional neutralisation assay against the challenge strain (BVDV-2 HI916) was performed Controls:
Clinical Signs and Blood Picture:
biphasic rise in their body temperatures: a slight one at day 3 and a pronounced one at days 7 and 8 p. chall. with maximum mean group values of up to 40.1° C.
showed typical and clear signs of clinical disease: distinct rise in clinical scores peaking at days 8 to 11: marked respiratory symptoms (coughing and mucopurulent nasal discharge), depression with reduced appetite (pronounced in 2 animals)
developed a severe leukopaenia: triphasic decrease (days 3, 7 and 11 p. chall.) in leukocyte counts with maximum levels of 44% reduction at day 3 p. chall.
thrombocyte counts: reduction over 9 days following challenge to a maximum of 48% at day 9 p. chall. counts quickly increased afterwards acute to mean values of 115% at the end of the trial
Virus Isolation:
challenge virus was detectable in the nasal swab samples of all control animals on day 2 and 3 and day 5 till 13—challenge virus viremia for up to 12 days (day 2-day 13)
Serology:
all control animals scored positive in the NS3 blocking ELISA from day 14 p. chall. on
detectable neutralising titres from day 14 post challenge against all strains, higher titres against BVDV-2 strains cp7 ΔNpro_E2CS8644

Clinical Signs and Blood Picture:
body temperatures: single but pronounced rise peaking at day 7 with maximum mean group values of up to 40.5° C.
no peak or clear rise of clinical scores compared to the vaccination period levels
leukocyte counts: single decline (22% on day 3 post challenge); quickly recovering to their pre-vaccination levels again (day 7 post challenge)
thrombocyte counts: reduction over 7 days following challenge; maximum of 19% at day 7 p. chall. counts quickly increased afterwards
Virus Isolation:
challenge virus shedding: 2 animals on day 3—challenge virus viremia in 2 animals for 1-2 days (day 3 to 5)
Serology:
NS3 blocking ELISA (Prionics) clear boost, blocking values of about 100% at the end of the trial
neutralising antibodies against BVDV-1 (cp7) and BVDV-2 (CS8644 and HI916) were boostered; titres against BVDV-1 stayed lower than in the mixed application group cp7 ΔNpro_E2CS8644+cp7ΔNpro
Clinical Signs and Blood Picture:
body temperatures: single rise peaking at day 7 with maximum mean group values of up to 39.6° C.
no peak or clear rise of clinical scores compared to the vaccination period levels
leukocyte counts: single decline (15% on day 4 post challenge); quickly recovering to their pre-vaccination levels again (day 7 post challenge)
thrombocyte counts: reduction over 7 days following challenge; maximum of 22% at day 7 p. chall. counts quickly increased afterwards
Virus Isolation:
neither challenge virus shedding nor challenge virus viremia could be observed
Serology:
NS3 blocking ELISA (Prionics) clear boost, blocking values of about 100% at the end of the trial
neutralising antibodies against BVDV-1 (cp7) and BVDV-2 (CS8644 and HI916) were boostered; titres against BVDV-1 higher than in the group receiving only the chimera Conclusions:
Although a very mild clinical reaction could be seen in both vaccinated groups after challenge infection (cp7ΔNpro_E2CS8644 fever, while in the group with the mixed application only raised temperature), vaccination with cp7ΔN$^{pro}$_E2CS8644+cp7ΔN$^{pro}$ in one single application led to a sterile immunity after challenge infection.

---

The invention claimed is:

1. A combination vaccine for the protection against Bovine Viral Diarrhea Virus (BVDV) that comprises a first live attenuated BVDV, a second live attenuated BVDV, and a pharmaceutically acceptable carrier;
   wherein the first BVDV and the second BVDV are either both Type 1 BVDVs or both Type 2 BVDVs;
   wherein the first BVDV and the second BVDV each comprise a BVDV E2 gene; and
   wherein when the first BVDV and the second BVDV are both Type 1 BVDVs, the E2 gene of the second BVDV is replaced by a BVDV E2 gene of a Type 2 BVDV; and wherein when the first BVDV and the second BVDV are both Type 2 BVDVs, the E2 gene of the second BVDV is replaced by a BVDV E2 gene of a Type 1 BVDV.

2. A combination vaccine for the protection against Bovine Viral Diarrhea Virus (BVDV) that comprises a first live attenuated BVDV, a second live attenuated BVDV, and a pharmaceutically acceptable carrier;
   wherein the first BVDV and the second BVDV are either both Type 1 BVDVs or both Type 2 BVDVs;
   wherein the first BVDV and the second BVDV each comprise a BVDV E1 gene and a BVDV E2 gene; and
   wherein when the first BVDV and the second BVDV are both Type 1 BVDVs, both the BVDV E2 gene and the BVDV E1 gene of the second BVDV are replaced by a BVDV E2 gene and a BVDV E1 gene of a Type 2 BVDV; and wherein when the first BVDV and the second BVDV are both Type 2 BVDVs, both the E2 and the E1 gene of the second BVDV is replaced by a BVDV E2 and BVDV E1 gene of a Type 1 BVDV.

3. The combination vaccine according to claim 1, wherein the backbone of the first and second BVDV belongs to a Type 1 BVDV and the BVDV E2 gene of the second BVDV belongs to a Type 2 BVDV.

4. The combination vaccine according to claim 1, wherein the backbone of the first and second BVDV belongs to a Type 2 BVDV and the BVDV E2 gene of the second BVDV belongs to a Type 1 BVDV.

5. The combination vaccine according to claim 1, characterised in that said first BVDV and said second BVDV have the same backbone.

6. The combination vaccine according to claim 5, characterised in that said backbone is BNDV a Type 1 BVDV.

7. The combination vaccine according to claim 1, wherein said first BVDV or said second BVDV comprises a deletion in a gene selected from the group consisting of the $N^{pro}$ gene and the $E^{rns}$ gene.

8. The combination vaccine according to claim 1, characterized in that said vaccine or combination vaccine comprises an additional antigen of a virus or micro-organism pathogenic to ruminants, an antibody against said antigen or genetic information encoding an immunogenic polypeptide of said virus or micro-organism.

9. The combination vaccine according to claim 8, characterized in that said virus or micro-organism pathogenic to ruminants is selected from the group of Bovine Rotavirus, Bovine Herpesvirus, Parainfluenza Type 3 virus, Bovine Paramyxovirus, Bluetongue virus, Foot and Mouth Disease virus, *Pasteurella haemolytica* and Bovine Respiratory Syncytial Virus.

10. The combination vaccine according to claim 1, characterised in that it is in a freeze-dried form.

11. A method for making a combination vaccine according to claim 1, comprising the step of mixing a live attenuated Type 1 BVDV that comprises a Type 1 BVDV E2 gene, a live attenuated Type 1 BVDV that comprises a Type 2 BVDV E2 gene in place of a Type 1 BVDV E2 gene, and a pharmaceutically acceptable carrier.

12. The combination vaccine according to claim 2, wherein the backbone of the first and second BVD virus belongs to a Type 1 BVDV and the BVDV E2 gene of the second BVD virus belongs to a Type 2 BVDV.

13. The combination vaccine according to claim 12, wherein said first BVDV and said second BVDV have the same backbone.

14. The combination vaccine according to claim 13, wherein said first BVDV or said second BVDV comprises a deletion in a gene selected from the group consisting of the $N^{pro}$ gene and the $E^{rns}$ gene.

15. The combination vaccine according to claim 2, characterised in wherein the backbone of the first and second BVD virus belongs to a Type 2 BVDV and the BVDV E2 gene and E1 gene of the second BVD virus belongs to a Type 1 BVDV.

16. A method for making a combination vaccine according to claim 1, comprising the step of mixing a live attenuated Type 2 BVDV that comprises a Type 2 BVDV E2 gene, a live attenuated Type 2 BVDV that comprises a Type 1 BVDV E2 gene in place of a Type 2 BVDV E2 gene, and a pharmaceutically acceptable carrier.

* * * * *

```
                       SEQUENCE LISTING

<160> NUMBER OF SEQ ID NOS: 9

<210> SEQ ID NO 1
<211> LENGTH: 33
<212> TYPE: DNA
<213> ORGANISM: bovine viral diarrhoea virus

<400> SEQUENCE: 1 acagggcgc aaggatatcc agactgcaaa ccc                           33

<210> SEQ ID NO 2
<211> LENGTH: 33
<212> TYPE: DNA
<213> ORGANISM: bovine viral diarrhoea virus

<400> SEQUENCE: 2
gggtttgcag tctggatatc cttgcgcccc tgt                          33

<210> SEQ ID NO 3
<211> LENGTH: 31
<212> TYPE: DNA
<213> ORGANISM: bovine viral diarrhoea virus

<400> SEQUENCE: 3
cggaagcagg aattaggttg gaaaaattac c                            31

<210> SEQ ID NO 4
<211> LENGTH: 24
<212> TYPE: DNA
<213> ORGANISM: bovine viral diarrhoea virus

<400> SEQUENCE: 4
cgtcactgta ggtgtgtctt aggc                                    24

<210> SEQ ID NO 5
<211> LENGTH: 21
<212> TYPE: DNA
<213> ORGANISM: bovine viral diarrhoea virus
```

```
<400> SEQUENCE: 5
gcaagaacta gcccagtcac g                                              21

<210> SEQ ID NO 6
<211> LENGTH: 34
<212> TYPE: DNA
<213> ORGANISM: bovine viral diarrhoea virus

<400> SEQUENCE: 6
ctagtggatc cccgggctg ttaaaggtct tccc                                 34

<210> SEQ ID NO 7
<211> LENGTH: 43
<212> TYPE: DNA
<213> ORGANISM: bovine viral diarrhoea virus

<400> SEQUENCE: 7
gctcataaca ggggcgcaag ggattccctg aatgcaaaga ggg                      43

<210> SEQ ID NO 8
<211> LENGTH: 41
<212> TYPE: DNA
<213> ORGANISM: bovine viral diarrhoea virus

<400> SEQUENCE: 8
cacctgcccc atactggaca cctatagcta cttgctctga c                        41

<210> SEQ ID NO 9
<211> LENGTH: 41
<212> TYPE: DNA
<213> ORGANISM: bovine viral diarrhoea virus

<400> SEQUENCE: 9
catggtttgg ggcatatgca gcaagtccat actgtgatgt g                        41
```

UNITED STATES PATENT AND TRADEMARK OFFICE
CERTIFICATE OF CORRECTION

| | | |
|---|---|---|
| PATENT NO. | : 9,878,030 B2 | Page 1 of 1 |
| APPLICATION NO. | : 13/825050 | |
| DATED | : January 30, 2018 | |
| INVENTOR(S) | : Beer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Eighth Day of May, 2018

Andrei Iancu
*Director of the United States Patent and Trademark Office*